US012741148B2

(12) United States Patent
Starr et al.

(10) Patent No.: US 12,741,148 B2
(45) Date of Patent: Sep. 22, 2026

(54) METHODS AND SYSTEMS FOR TREATING NEUROLOGICAL MOVEMENT DISORDERS

(71) Applicant: The Regents of the University of California, Oakland, CA (US)

(72) Inventors: Philip A. Starr, Mill Valley, CA (US); Nicole Swann, El Cerrito, CA (US); Coralie de Hemptinne, San Francisco, CA (US); Jill Ostrem, Greenbrae, CA (US)

(73) Assignee: The Regents of the University of California, Oakland, CA (US)

( * ) Notice: Subject to any disclaimer, the term of this patent is extended or adjusted under 35 U.S.C. 154(b) by 473 days.

(21) Appl. No.: 15/577,681

(22) PCT Filed: Jun. 3, 2016

(86) PCT No.: PCT/US2016/035845
§ 371 (c)(1),
(2) Date: Nov. 28, 2017

(87) PCT Pub. No.: WO2016/197007
PCT Pub. Date: Dec. 8, 2016

(65) Prior Publication Data

US 2018/0353759 A1 Dec. 13, 2018

Related U.S. Application Data

(60) Provisional application No. 62/171,079, filed on Jun. 4, 2015.

(51) Int. Cl.
*A61B 5/00* (2006.01)
*A61B 5/37* (2021.01)
(Continued)

(52) U.S. Cl.
CPC ............ *A61N 1/36139* (2013.01); *A61B 5/37* (2021.01); *A61B 5/372* (2021.01); *A61B 5/4082* (2013.01);
(Continued)

(58) Field of Classification Search
None
See application file for complete search history.

(56) References Cited

U.S. PATENT DOCUMENTS 5,716,377 A 2/1998 Rise et al.
5,843,148 A 12/1998 Gijsbers et al.
(Continued)

FOREIGN PATENT DOCUMENTS

WO WO-2015070281 A1 * 5/2015 .......... A61B 5/4839

OTHER PUBLICATIONS

Halje, P., Tamte, M., Richter, U., Mohammed, M., Cenci, M. A., Petersson, P. (2012). Levodopa-Induced Dyskinesia Is Strongly Associated with Resonant Cortical Oscillations. Journal of Neuroscience, 32(47), 16541-16551. doi:10.1523/jneurosci.3047-12.2012 (Year: 2012).*

(Continued)

*Primary Examiner* — Etsub D Berhanu
(74) *Attorney, Agent, or Firm* — Edward J. Baba; Michael J. Blessent; Bozicevic, Field & Francis LLP

(57) ABSTRACT

The present disclosure provides methods for detecting hyperkinetic state by measuring brain activity of a patient suffering from a movement disorder. Also provided are methods for modulating therapy in patients suffering from a movement disorder. Aspects of the methods include measuring activity in brain of the patient and changing a treatment regimen if hyperkinetic state is detected. Also provided are devices, systems, and kits that may be used in practicing the subject methods.

14 Claims, 23 Drawing Sheets

(51) Int. Cl.
*A61B 5/372* (2021.01)
*A61B 5/374* (2021.01)
*A61N 1/36* (2006.01)
*A61N 1/05* (2006.01)

(52) U.S. Cl.
CPC ..... *A61N 1/36067* (2013.01); *A61N 1/36146* (2013.01); *A61B 5/4848* (2013.01); *A61N 1/0534* (2013.01)

(56) References Cited

U.S. PATENT DOCUMENTS

| | | | | |
|---|---|---|---|---|
| 6,066,163 | A | 5/2000 | John | |
| 6,253,109 | B1 | 6/2001 | Gielen | |
| 6,463,328 | B1 | 10/2002 | John | |
| 6,484,059 | B2 | 11/2002 | Gielen | |
| 6,539,263 | B1 | 3/2003 | Schiff et al. | |
| 6,587,724 | B2 | 7/2003 | Mann | |
| 6,920,359 | B2 | 7/2005 | Meadows et al. | |
| 7,003,352 | B1 | 2/2006 | Whitehurst | |
| 7,033,326 | B1 | 4/2006 | Pianca et al. | |
| 7,149,574 | B2 | 12/2006 | Yun et al. | |
| 7,151,961 | B1 | 12/2006 | Whitehurst et al. | |
| 7,212,867 | B2 | 5/2007 | Van Venroo et al. | |
| 7,295,880 | B2 | 11/2007 | Gielen | |
| 7,346,382 | B2 | 3/2008 | McIntyre et al. | |
| 7,369,899 | B2 | 5/2008 | Malinowski et al. | |
| 7,539,543 | B2 | 5/2009 | Schiff et al. | |
| 7,809,446 | B2 | 10/2010 | Meadows | |
| 7,904,134 | B2 | 3/2011 | McIntyre et al. | |
| 7,957,808 | B2 | 6/2011 | Dawant et al. | |
| 2005/0277995 | A1* | 12/2005 | Gill | A61N 1/36067 607/45 |
| 2006/0017749 | A1* | 1/2006 | McIntyre | A61N 1/36082 345/664 |
| 2006/0106431 | A1* | 5/2006 | Wyler | A61N 1/36067 607/48 |
| 2006/0173509 | A1 | 8/2006 | Lee et al. | |
| 2007/0225674 | A1* | 9/2007 | Molnar | A61N 1/36067 604/503 |
| 2009/0248113 | A1* | 10/2009 | Nimer | A61N 1/05 607/60 |
| 2011/0184487 | A1* | 7/2011 | Alberts | A61N 1/0534 607/45 |
| 2011/0196446 | A1* | 8/2011 | Wu | A61N 1/36067 607/45 |
| 2014/0005743 | A1* | 1/2014 | Giuffrida | A61N 1/37247 607/45 |
| 2014/0163627 | A1* | 6/2014 | Starr | A61N 1/36067 607/3 |
| 2014/0350634 | A1* | 11/2014 | Grill | A61N 1/36067 607/45 |
| 2015/0202447 | A1* | 7/2015 | Afshar | A61N 1/36171 600/378 |

OTHER PUBLICATIONS

Benabid, A. L., Benazzouz, A., Limousin, P., Koudsie, A., Krack, P., Piallat, B., Pollak, P. (2000). Dyskinesias and the subthalamic nucleus [Abstract]. Annals of Neurology, 47(4), 1st ser., 189-192. doi:Sep. 24, 2020 (Year: 2000).*

Simonin et al. Reduced levodopa-induced complications after 5 years of subthalamic stimulation in Parkinson's disease: a second honeymoon. Journal of Neurology (2009) 256: 1736-1741. (Year: 2009).*

Giannicola et al. The effects of levodopa and ongoing deep brain stimulation on subthalamic beta oscillations in Parkinson's diease. Experimental Neurology 226 (2010) 120-127. (Year: 2010).*

Rizzone et al. Deep brain stimulation fo the sbuthalamic nucleus in Parkinson's disease: effects of variation in stimulation parameters. Journal of Neurology, Neurosurgery, and Psychiatry, 2001; 71:215-219. (Year: 2001).*

Alegre et al., (2012) "Subthalamic Activity During Diphasic Dyskinesias in Parkinson's Disease" Movement Disorders 27: 1178-1181.

Alonso-Frech et al., (2006) "Slow oscillatory activity and levodopa-induced dyskinesias in Parkinson's disease", Brain 129: 1748-1757.

Bastide et al., (2015) "Pathophysiology of L-dopa-induced motor and non-motor complications in Parkinson's disease", Progress Neurobiology 132: 96-168.

Cagnan et al., (2014) "Co-modulation of finely tuned high-gamma band activity across hemispheres in Parkinson's disease", Clin Neurophysiol 125: 777-785.

Carta et al., (2007) "Dopamine released from 5-HT terminals is the cause of L-DOPA-induced dyskinesia in parkinsonian rats", Brain 130: 1819-1833.

Cassidy et al., (2002) "Movement-related changes in synchronization in the human basal ganglia", Brain 125: 1235-1246.

Crone et al., (1998) "Functional mapping of human sensorimotor cortex with electrocorticographic spectral analysis I. Alpha and beta event-related desynchronization", Brain 121: 2271-2299.

Crone et al., (1998) "Functional mapping of human sensorimotor cortex with electrocorticographic spectral analysis II. Event-related synchronization in the gamma band", Brain 121: 2301-2315.

Crowell et al., (2012) "Oscillations in sensorimotor cortex in movement disorders: an electrocorticography study", Brain 135(Pt 2): 615-630.

De Hemptinne et al., (2013) "Exaggerated phase-amplitude coupling in the primary motor cortex in Parkinson disease", PNAS 110(12): 4780-4785.

De Hemptinne et al., (2015) "Therapeutic deep brain stimulation reduces cortical phaseamplitude coupling in Parkinson's disease", Nat Neurosci 18(5): 779-786.

Fieblinger et al., (2015), "Zooming in on the small: The plasticity of striatal dendritic spines in I-DOPA-Induced dyskinesia", Movement Disorders 30: 484-493.

Garcia et al., (2003) "Dual Effect of High-Frequency Stimulation on Subthalamic Neuron Activity", The Journal of Neuroscience 23: 8743-8751.

Goetz et al., (2008) "The Unified Dyskinesia Rating Scale: Presentationand Clinimetric Profile", Movement Disorder Society 23: 2398-2403.

Graziano et al., (2002) "Complex Movements Evoked by Microstimulation of Precentral Cortex", Neuron 34: 841-851.

Halje et al., (2012) "Levodopa-Induced Dyskinesia Is Strongly Associated with Resonant Cortical Oscillations", The Journal of Neuroscience 32(47): 16541-16551.

Hammond et al., (2007), "Pathological synchronization in Parkinson's disease: networks, models and treatments", Trends Neurosciences 30: 357-364.

Hashimoto et al., (2003), "Stimulation of the Subthalamic Nucleus Changes the Firing Pattern of Pallidal Neurons", The Journal Neuroscience 23: 1916-1923.

Hatsopoulos et al., (2007) "Encoding of Movement Fragments in the Motor Cortex", The Journal of Neuroscience 27: 5105-5114.

Li et al., (2012) "Therapeutic Deep Brain Stimulation in Parkinsonian Rats Directly Influences Motor Cortex", Neuron 76: 1030-1041.

Little et al., (2013), "Adaptive Deep Brain Stimulation in Advanced Parkinson Disease," Annals of neurology 74: 449-457.

Mallet et al., (2008), "Subthalamic Nucleus Stimulation in Severe Obsessive-Compulsive Disorder," The New England journal of medicine 359: 2121-2134.

Manning et al., (2009) "Broadband Shifts in Local Field Potential Power Spectra Are Correlated with Single-Neuron Spiking in Humans ", The Journal of Neuroscience 29: 13613-13620.

Miller et al., (2007) "Spectral Changes in Cortical Surface Potentials during Motor Movement", Journal of Neuroscience 27: 2424-2432.

Mouton et al., (2006), "Chorea Induced by Globus Pallidus Externus Stimulation in a Dystonic Patient", Movement Disorders 21: 1771-1773.

Ostrem et al., (2011) "Subthalamic nucleus deep brain stimulation in primary cervical dystonia", Neurology 76(10): 870-878.

(56) References Cited

OTHER PUBLICATIONS

Oyama et al., (2012) "GPi and STN deep brain stimulation can suppress dyskinesia in Parkinson's disease", Parkinsonism & Related Disorders 18: 814-818.
Pritchard (1992), "The Brain in Fractal Time: 1/F-Like Power Spectrum Scaling of the Human Electroencephalogram", Int J Neurosci 66: 119-129.
Puig et al., (2010) "Serotonin Modulates Fast-Spiking Interneuron and Synchronous Activity in the Rat Prefrontal Cortex through 5-HT1A and 5-HT2A Receptors", The Journal of Neuroscience 30: 2211-2222.
Ray et al., (2008) "Neural Correlates of High-Gamma Oscillations (60-200 Hz) in Macaque Local Field Potentials and Their Potential Implications in Electrocorticography", The Journal of Neuroscience 28: 11526-11536.
Rosin et al., (2011) "Closed-Loop Deep Brain Stimulation Is Superior in Ameliorating Parkinsonism," Neuron 72: 370-384.
Rowland et al., (2015) "Task-related activity in sensorimotor cortex in Parkinson's disease and essential tremor: changes in beta and gamma bands", Frontiers in Human Neuroscience 9: 512.
Salkoff et al., (2015), "Synaptic Mechanisms of Tight Spike Synchrony at Gamma Frequency in Cerebral Cortex", The Journal of Neuroscience 35: 10236-10251.
Scheffer-Teixeira et al., (2013) "On High-Frequency Field Oscillations (100 Hz) and the Spectral Leakage of Spiking Activity", The Journal Neuroscience 33: 1535-1539.
Shahlaie et al., (2011) "Intraoperative Computed Tomography for Deep Brain Stimulation Surgery: Technique and Accuracy Assessment", Operative Neurosurgery 68: 114-124.
Silberstein et al., (2005) "Cortico-cortical coupling in Parkinson's disease and its modulation by therapy", Brain 128: 1277-1291.
Sohal (2012) "Insights into Cortical Oscillations Arising from Optogenetic Studies", Biol Psychiatry 71: 1039-1045.
Starr et al., (2002) "Implantation of deep brain stimulators into the subthalamic nucleus: technical approach and magnetic resonance imaging-verified lead locations", Journal of Neurosurgery 97:370-387.
Teles-Grilo Ruivo et al., (2013), "Cholinergic modulation of hippocampal network function", The Frontiers in Synaptic Neurosci 5: Article 2.
Thiele et al., (2014) "Selective loss of bi-directional synaptic plasticity in the direct and indirect striatal output pathways accompanies generation of parkinsonism and I-DOPA induced dyskinesia in mouse models", Neurobiology of disease 71: 334-344.
Trottenberg et al., (2006) "Subthalamic gamma activity in patients with Parkinson's disease", Experimental neurology 200: 56-65.
Voytek et al., (2015), "Dynamic Network Communication as a Unifying Neural Basis for Cognition, Development, Aging, and Disease", Biological Psychiatry 77: 1089-1097.
Weinberger et al., (2011), "A basis for the pathological oscillations in basal ganglia: the crucial role of dopamine", Neuroreport 22: 151-156.
Weinberger et al., (2012) "Oscillatory activity in the globus pallidus internus: Comparison between Parkinson's disease and dystonia", Clinical Neurophysiology 123: 358-368.
Williams et al., (2002) "Dopamine-dependent changes in the functional connectivity between basal ganglia and cerebral cortex in humans", Brain 125: 1558-1569.
Yizhar et al., (2011), "Neocortical excitation/inhibition balance in information processing and social dysfunction", Nature 477: 171-178.
Yousry et al., (1997), "Localization of the motor hand area to a knob on the precentral gyrus", Brain 120(Pt 1): 141-157.
Zheng et al., (2010) "Stimulation-Induced Dyskinesia in the Early Stage after Subthalamic Deep Brain Stimulation", Stereotact Funct Neurosurg 88: 29-34.
Zweig et al., (1993), "Receiver-Operating Characteristic (ROC) Plots: A Fundamental Evaluation Tool in Clinical Medicine", Clin. Chem. 39(4): 561-577.

* cited by examiner

A
Motor cortex PSD
Dyskinesia
No dyskinesia
PSD
10
0
-10
-20
20
60
100
140
Frequency (Hz)
Coherence
Dyskinesia
No dyskinesia
Coherence
0.4
0.2
0
20
60
100
Frequency (Hz)
STN PSD
PSD
5
0
-5
-10
-15
-20
20
60
100
140
Frequency (Hz)
Phase coherence
Coherence
0.4
0.2
0
20
60
100
Frequency (Hz)

B

2. Flattened and normalized PSD to find peak frequency in 62-83 Hz range

Normalized and flattened PSD

Frequency (Hz)

C

A. Patient 1

Coherence
0
0.1
0.2
0.3
0.4
0.5
p=0.08
No dyskinesia
Dyskinesia

Phase Coherence
0
0.1
0.2
0.3
**
No dyskinesia
Dyskinesia

B. Patient 2

Phase Coherence
Area under the curve: 0.801
True positive rate
False positive rate

A

All recordings - distribution of phase angle differences

B

Only DBS off - distribution of phase angle differences

Beta - Off DBS

Figure 11:
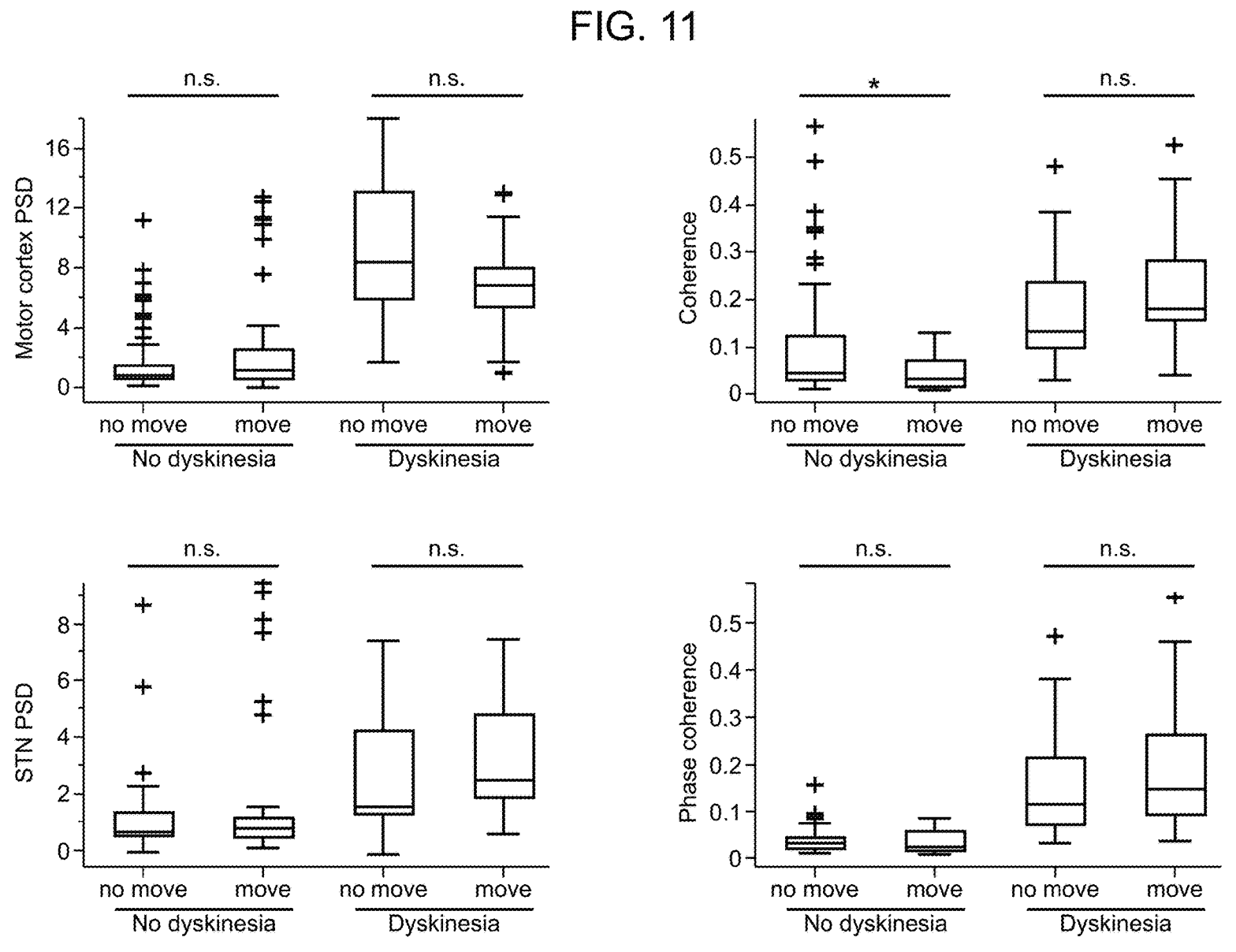

Motor cortex PSD
16
12
8
4
0
n.s.
n.s.
no move
move
no move
move
No dyskinesia
Dyskinesia Coherence
0.5
0.4
0.3
0.2
0.1
0
*
n.s.
no move
move
no move
move
No dyskinesia
Dyskinesia STN PSD
8
6
4
2
0
n.s.
n.s.
no move
move
no move
move
No dyskinesia
Dyskinesia Phase coherence
0.5
0.4
0.3
0.2
0.1
0
n.s.
n.s.
no move
move
no move
move
No dyskinesia
Dyskinesia A
160 Hz stimulation
Dyskinesia / on DBS
No dyskinesia / off DBS
80 Hz
motor cortex PSD
Frequency (Hz)
B
130 Hz stimulation
Dyskinesia / on DBS
No dyskinesia / on DBS
65 Hz
motor cortex PSD
Frequency (Hz)
C
Changing from 130 Hz stimulation to 150 Hz
150 Hz stimulation
130 Hz stimulation
65 Hz
75 Hz
motor cortex PSD
Frequency (Hz)

D

PHASE ANGLE ON DBS

Phase difference at 7th folded harmonic of stimulation (116 Hz)

E
WASH IN
DBS Off
-3 to -2 min
-2 to -1 min
-1 to 0 min
PSD
5
0
-5
-10
65
75
85
Frequency (Hz)
DBS On
0 to 1 min
1 to 2 min
2 to 3 min
3 to 4 min
4 to 5 min

METHODS AND SYSTEMS FOR TREATING NEUROLOGICAL MOVEMENT DISORDERS

CROSS-REFERENCE TO RELATED APPLICATIONS

This application claims priority benefit of U.S. provisional application Ser. No. 62/171,079 filed Jun. 4, 2015 which application is herein incorporated by reference in its entirety.

STATEMENT REGARDING FEDERALLY SPONSORED RESEARCH

This invention was made with government support under Grant No. R01 NS090913 awarded by the National Institutes of Health. The government has certain rights in the invention.

INTRODUCTION

Hyperkinetic states are common in human neurological disorders. Hyperkinetic state refers a state of excessive restlessness, an increase in muscular activity that can result in excessive movements. Hyperkinetic state is associated in a large variety of disorders that affect the ability to control motor movement and can also be detected in disorders that overall are marked by hypokinesia, such as Parkinson's disease.

Other disorders having hyperkinetic states include dyskinesia, essential tremor, dystonia, Huntington's disease, Tourette syndrome, and the like. Dyskinesias are involuntary movements which can be uncomfortable, socially stigmatizing, and even dangerous over time. Dyskinesias often occur in Parkinson's disease (PD) patients after prolonged treatment with medications such as levodopa. PD is the second most common neurological movement disorder, affecting approximately 0.5% of the population.

For many patients suffering from the clinical presentations of a neurological movement disorder, including those with mid-stage PD that is no longer optimally improved by medication, the treatment of choice is chronic deep brain stimulation (DBS) of structures located in the basal ganglia. However, DBS can also induce dyskinesia. While movement disorders afflict a wide population, their neural basis remains uncertain.

SUMMARY

The present disclosure provides methods for detecting hyperkinetic state in a human patient by measuring brain activity in the patient. The patient may be suffering from a disorder such as a neurological disorder and receiving a treatment for the disorder. Aspects of the methods include changing a treatment regimen for the disorder upon detection of the hyperkinetic state in the patient.

In certain cases, the treatment may cause hyperkinetic state in the patient. In these cases, the treatment may be changed upon detection of hyperkinetic state.

In certain cases, one or more methods for detecting hyperkinetic state in a patient having a neurological disorder and changing a treatment of the neurological disorder may be performed using a closed loop system.

In certain aspects, a method of treating a movement disorder in a human patient may include measuring oscillatory activity in brain of the patient, wherein the patient is receiving a treatment for the movement disorder; modifying the treatment of the patient when an oscillatory activity in the range of 60 Hz-90 Hz is measured, wherein oscillatory activity in the range of 60 Hz-90 Hz is indicative of hyperkinetic state in the patient, wherein the treatment comprises deep brain stimulation (DBS) and/or a medication regimen, wherein modifying the treatment comprises adjusting a parameter of DBS and/or changing the medication regimen.

In certain cases, the modifying the treatment comprises adjusting a parameter of DBS and/or changing the medication regimen may be performed till at least the oscillatory activity indicative of hyperkinetic state is reduced or removed.

In certain cases, the oscillatory activity may include field potential or may be derived from field potential recordings. In certain cases, measuring oscillatory activity may include chronic electrocorticography (ECoG). In certain cases, the oscillatory activity may be recorded from a region of the brain, such as, motor cortex, primary motor cortex (M1), subdural space over the primary motor cortex (M1), subthalamic nucleus (e.g., dorsal or ventral STN), thalamus, basal ganglia, nuclei from basal ganglia thalamo cortical loop, striatum, globus pallidus (GP), and/or any region connected to the STN and motor cortex.

In certain aspects, the human patient may have a neurological disease that may be associated with hyperkinesia. In certain aspects, the human patient may have Parkinson's disease, primary or secondary dystonia, dyskinesia, Huntington's disease, essential tremor, Tourette syndrome, mood disorders, obsessive compulsive disorder, psychotic disorders, and other psychiatric conditions.

In certain cases, the patient may be receiving treatment (e.g., DBS and/or medication) for Parkinson's disease. For example, the PD patient may be receiving DBS. Upon detection of oscillatory activity in the range of 60 Hz-90 Hz, the DBS may be modified to prevent recurrence of the oscillatory activity in the range of 60 Hz-90 Hz. In certain cases, PD patient may be receiving a medication for treatment of PD. In certain cases, the medication may be levodopa. Upon detection of oscillatory activity in the range of 60 Hz-90 Hz, the dose of the medication may be reduced or the patient may be administered a different medication.

In certain cases, the patient may have dystonia and may be receiving a treatment for dystonia. The treatment may be DBS and/or medication. Upon detection of oscillatory activity in the range of 60 Hz-90 Hz, the DBS or a medication regimen for treatment of dystonia may be changed. For example, the dosage of the medication may be increased. The medication may be one or more of anticholinergics, bendiazepines, baclofen, dopaminergic agent, and tetrabenezine.

In certain aspects, a method for detecting hyperkinetic state in a human patient is disclosed. The method includes measuring oscillatory activity in brain of the patient; wherein presence of oscillatory activity in the range of 60 Hz-90 Hz indicates the presence of hyperkinetic state in the patient. In certain aspects, patient may have a neurological disorder as provided herein.

In another aspect, a method for detecting hyperkinetic state in a human patient receiving DBS is disclosed. The method includes administering deep brain stimulation (DBS) at a first frequency to the patient; measuring oscillatory activity in brain of the patient; wherein presence of oscillatory activity at a frequency approximately half of the first frequency indicates the presence of hyperkinetic state in the patient. In certain cases, the DBS is in the range of 120 Hz-180 Hz and the oscillatory activity is in the range of 60

Hz-90 Hz or the DBS is in the range of 130 Hz-150 Hz and the oscillatory activity is in the range of 65 Hz-75 Hz.

In certain embodiments, methods of the present disclosure include a method for treating Parkinson's disease in a human patient. The method may include measuring oscillatory activity in brain of the patient receiving a treatment for Parkinson's disease; modifying the treatment of the patient when an oscillatory activity in the range of 60 Hz-90 Hz is measured, where the treatment includes deep brain stimulation (DBS) and/or medication, where modifying the treatment includes adjusting a parameter of DBS and/or changing medication regimen. In certain cases, the oscillatory activity may be measured via local field potentials (LFPs). In certain cases, the oscillatory activity may be measured with electrocorticography (ECoG). In certain aspects, the method may include measuring oscillatory activity in or near primary motor cortex, such as, in the subdural space over the primary motor cortex. In certain cases, the Parkinson's disease patient may be receiving DBS and the measured oscillatory activity in brain of the patient may be at a frequency approximately half of the frequency of the DBS frequency. The DBS frequency may range from 200 Hz-50 Hz and the measured oscillatory activity in brain of the patient may be at a frequency approximately half of the frequency of the DBS frequency indicates hyperkinesia in the patient. In certain cases, the Parkinson's disease patient may be receiving DBS in the range of 120 Hz-180 Hz, and the presence of oscillatory activity in the range of 60 Hz-90 Hz in brain of the patient indicates that a parameter of the DBS should be adjusted. The oscillatory activity may be recorded from a region of the brain, for example, from one or more of motor cortex, primary motor cortex (M1), subdural space over the primary motor cortex (M1), subthalamic nucleus (e.g., dorsal or ventral STN), thalamus, basal ganglia, nuclei from basal ganglia thalamo cortical loop, striatum, globus pallidus (GP), and/or any region connected to the STN and motor cortex.

In certain cases, the Parkinson's disease patient may be receiving treatment that includes DBS and the parameter of DBS may be selected from the group consisting of contact choice, amplitude, pulse width, and frequency of stimulation. In certain cases, changing DBS parameter may include stimulating the dorsal STN, for example, via a most dorsal STN contact connected to a DBS device.

In certain cases, the treatment may include administering a medication for Parkinson's disease and changing the medication regimen may include lowering dosage of the medication (e.g., withholding the next scheduled administration of the medication or administering a lower dose of the medication) or using a different medication. In certain cases, the medication may be levodopa.

Also disclosed herein are methods for improving treatment of a neurological disorder in the human patient, where the treatment has a side-effect of inducing a hyperkinetic state in the patient. In certain cases, the treatment may be deep brain stimulation that may be leading to development of hyperkinetic state in the patient receiving the DBS. The subject methods may be used for detecting hyperkinetic state by determining the presence of an oscillatory activity in the brain (for example, in motor cortex or the STN) of the patient receiving a DBS, where the oscillatory activity is about half the frequency of the DBS and changing a parameter of the DBS to treat the hyperkinetic state. In certain cases, the subject methods may be used for detecting hyperkinetic state by determining the presence of an oscillatory activity in the range of 60 Hz-90 Hz from the brain of the patient receiving a DBS in the range of 120 Hz-180 Hz and changing a parameter of the DBS to prevent hyperkinesia. For example, the parameter may be amplitude (current or voltage), pulse width, or frequency of stimulation and the parameter may be reduced to prevent hyperkinesia. In other cases, the location of delivery of DBS may be switched by activating a different contact on an array of electrodes positioned in the brain, for example, stimulation may be switched to dorsal STN.

Methods of the present disclosure may be used for detecting hyperkinetic state in a human patient, the method comprising measuring oscillatory activity in brain of the patient; wherein presence of oscillatory activity in the range of 60 Hz-90 Hz, and/or, if during DBS, at half the frequency that DBS is delivered, indicates the presence of hyperkinetic state in the patient. In some cases, the patient may have been diagnosed as suffering from a neurological disorder. In some cases, the patient may be receiving treatment for the neurological disorder. In some cases, the treatment (such as medication or DBS) for the movement disorder may be causing the hyperkinetic state.

Also provided herein are devices and systems that carry out the methods of the present disclosure. In certain aspects, a system for managing treatment of a neurological disorder in a human patient is provided. The system may include an input configured for receiving data comprising oscillatory activity recorded from a desired region of the brain (e.g., from primary motor cortex, subdural space over the primary motor cortex, or subthalamic nucleus); an output in electronic communication with i) a pulse generator for administering DBS; ii) a display for displaying instructions to adjust a medication; or iii) a device for administering medication; a processor in electronic communication with the input and the output, the processor programmed to execute instructions to: change a parameter of the pulse generator upon detecting an oscillatory activity in the range of 60 Hz-90 Hz, and/or at half the frequency that DBS is delivered, being received by the input, and/or display instructions on the display to decrease or withhold next administration of the medication upon detecting an oscillatory activity in the range of 60 Hz-90 Hz, and/or, if during DBS, at half the frequency that DBS is delivered, being received by the input, and/or change a parameter of the medication delivery device to withhold the next dose or reduce the next dose or to decrease the overall dose of the medication or to change the medication. The system may be configured to cycle though the steps of the methods of the present disclosure until the oscillatory activity indicative of hyperkinesia is no longer detected or is reduced. The system may include leads configured for implantation for providing deep brain stimulation to the patient. The processor is configured to execute instructions for changing the strength of the DBS to the patient when oscillatory activity in the range of 60 Hz-90 Hz, and/or, if during DBS, at half the frequency that DBS is delivered (e.g., 65 Hz frequency upon stimulation at 130 Hz or 75 Hz frequency upon stimulation with 150 Hz), is detected. The system may include an output for outputting instructions for a lowering of dose of a medication for treating the disorder. The system may change a parameter by the processor where the parameter is selected from the group consisting of contact choice, amplitude, and frequency. The system may be a closed loop system.

The oscillatory activity may be field potentials that may be measured using one or more electrodes, such as non-brain-penetrating electrodes or brain penetrating electrodes. In certain aspects, at least one electrode for measuring oscillatory activity is located at a position corresponding to the primary motor cortex (M1), subdural space over the primary motor cortex (M1), subthalamic nucleus (e.g., dorsal or ventral STN), thalamus, basal ganglia, nuclei from basal ganglia thalamo cortical loop, striatum, globus pallidus (GP), and/or any region connected to the STN and motor cortex. In some cases, a penetrating electrode may be positioned in the STN for measuring field potential.

In other embodiments, methods of the present disclosure include measuring field potentials using one or more of non-brain-penetrating electrode located at a position in or near the primary motor cortex M1 of the patient's brain (e.g., by electrocorticography (ECoG) using at least one ECoG electrode, or by electroencephalography (EEG) using at least one EEG electrode) and a penetrating electrode positioned in the STN, where the patient is being treated for movement disorder with DBS comprising a first deep brain stimulus; determining, with a processor, presence of field potentials in 60 Hz-90 Hz range, and/or, if during DBS, at half the frequency that DBS is delivered; and discontinuing administration of the first deep brain stimulus and administering a second deep brain stimulus to the subject if field potentials in 60 Hz-90 Hz range are detected, and/or, if during DBS, at half the frequency that DBS is delivered, are detected, wherein the second deep brain stimulus is different from the first deep brain stimulus; and said administering is in a manner effective to reduce field potentials in 60 Hz-90 Hz range, and/or, if during DBS, at half the frequency that DBS is delivered. Such methods may further include calculating, with the processor, at least one parameter of the first deep brain stimulus to change if the field potentials in 60 Hz-90 Hz range, and/or, if during DBS, at half the frequency that DBS is delivered, is detected; optionally receiving, via the processor, a user confirmation in response to a prompt to change said at least one parameter of the deep brain stimulus; and changing, with the processor, said at least one parameter of the deep brain stimulation; with such steps performed prior to administering the second (and subsequent) stimulus to the patient.

As noted herein, the detection of an activity in the range of 60 Hz-90 Hz, and/or, if during DBS, at half the frequency that DBS is delivered, may be used (e.g., by a processor) to cause one or more changes in the treatment of a human patient. For example, in certain embodiments the processor may change one or more parameters of a first deep brain stimulus prior to administering a second or subsequent brain stimulus if the measured activity is in the range of 60 Hz-90 Hz, and/or, if during DBS, at half the frequency that DBS is delivered. The parameters to be changed may include, but are not limited to, the contact choice, amplitude, and/or frequency of such deep brain stimulation. In certain cases, the contact choice may be changed. In certain cases, the amplitude, and/or frequency of the deep brain stimulation may be reduced. The change in the parameter may be for a period sufficient to reduce or remove hyperkinesia marked by the brain activity is in the range of 60 Hz-90 Hz.

In practicing the subject methods, the manner of administering deep brain stimulation may vary. For example, deep brain stimulation may include stimulating one or more portions of a subject's brain, such as the structures in the basal ganglia, including the subthalamic nucleus, the globus pallidus, and/or the like. Deep brain stimulation may be administered using one or more electrodes of an array. Stimulation electrodes may be arranged as a stimulation electrode array. Aspects of embodiments of the methods of the present disclosure include placing one or more electrodes, such as a stimulation electrode array, in the subject's brain so as to deliver deep brain stimulation.

In certain aspects, the patient may be undergoing treatment with a pharmacological. Pharmacological agents of interest include, but are not limited to, levodopa, carbidopa, catechol O-methyltransferase inhibitors, monoamine oxidase inhibitors, dopamine agonists, anticholinergics, catecholamines, baclofen, benzodiazepines, tetrabenezine, diazepam, clonazepam, and lorazepam. Administration of a pharmacological agent to a subject may be achieved in various ways, including, but not limited to, oral, parenteral (e.g., subcutaneous, intramuscular, intradermal, intravenous and intrathecal), intraperitoneal, intravesicular, etc., administration. In certain aspects, administration is controlled by a processor configured to administer the pharmacological agent (e.g., using a drug delivery device). The processor may change one or more parameters of such administration if the activity is in the range of 60 Hz-90 Hz, and/or, if during DBS, at half the frequency that DBS is delivered. For example, the processor may reduce administration frequency and/or amount of the pharmacological agent when oscillatory activity is in the range of 60 Hz-90 Hz is detected as explained herein, and/or, if during DBS, at half the frequency that DBS is delivered.

A wide variety of neurological conditions may be treated using methods of the present disclosure. In certain aspects, the subject exhibits clinical presentations of a neurological disorder, such as Parkinson's disease, dystonia, Huntington's disease, essential tremor, anxiety, mood disorders, obsessive compulsive disorders, and chronic pain disorders. Suitable subjects include those that have been diagnosed with a neurological disorder. Suitable subjects include those that have been diagnosed with a neurological disorder and are receiving treatment for the neurological disorder. Such a treatment may be pharmacological treatment, psychological treatment, deep brain stimulation, and combinations thereof. In certain cases, a patient being treated with DBS may suffer from hyperkinesia, such a patient may also be monitored using the methods of the present disclosure.

Also provided by the present disclosure are devices that may be used in practicing the subject methods. In certain embodiments, devices of the present disclosure include an input configured to receive field potentials (e.g., LFPs) from at least one electrode; an output configured to be in electronic communication with a pulse generator for administering deep brain stimulation; a processor in electronic communication with the input and the output, the processor programmed to respond to 70 Hz-90 Hz activity received from the input; and change at least one parameter of the pulse generator. A device may include a number of additional components, such as a display (e.g., a display including a user interface), drug delivery device, data logging element(s), and/or user input elements (e.g., buttons, dials, and the like).

Also provided are devices, systems, and kits for practicing the subject methods.

BRIEF DESCRIPTION OF THE DRAWINGS

The invention may be best understood from the following detailed description when read in conjunction with the accompanying drawings. Included in the drawings are the following figures:

FIG. 11 shows that amplitudes of dyskinesia biomarkers related to the gamma oscillation are minimally affected by voluntary movement.

DETAILED DESCRIPTION

Figure 1:
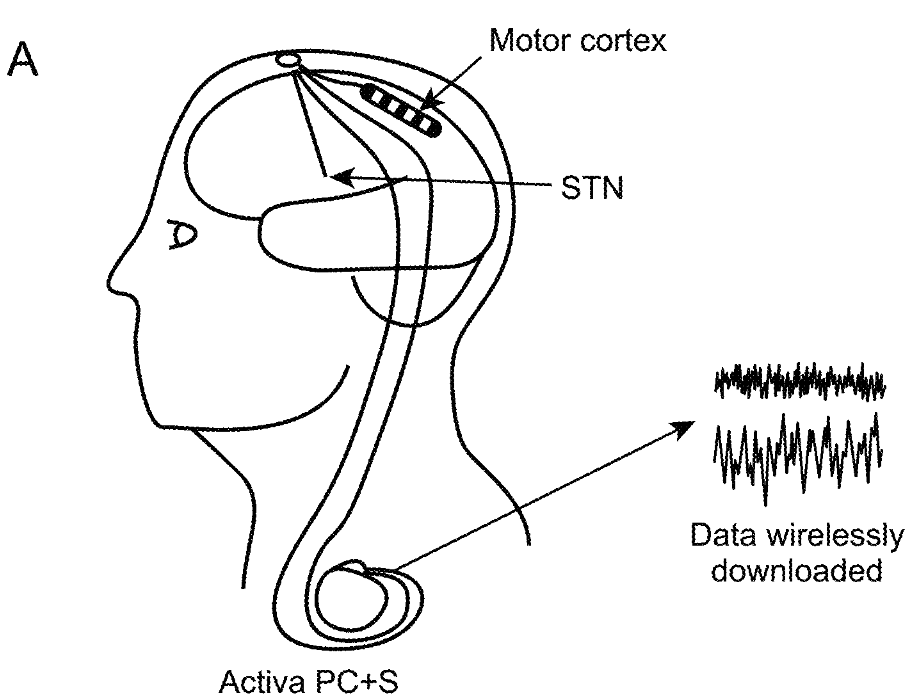
FIG. 1, Panels A-D illustrate electrode locations, raw signals, and signal stability over time.
Figure 1:
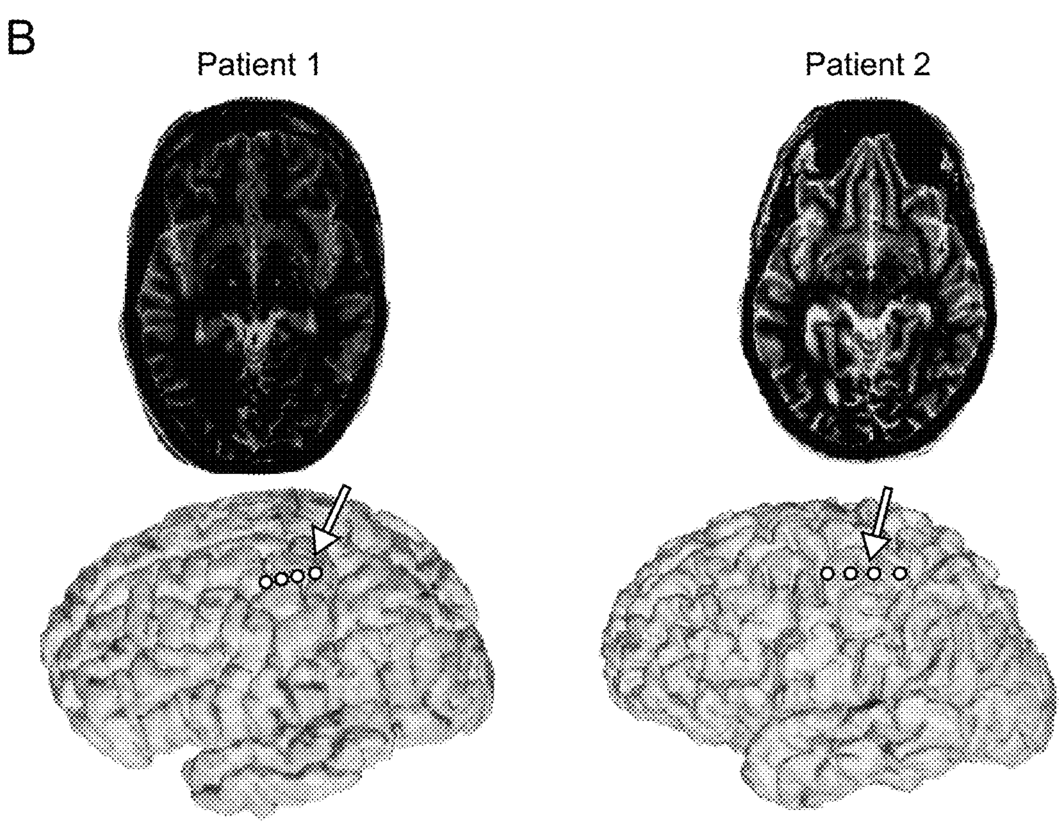
Figure 1:
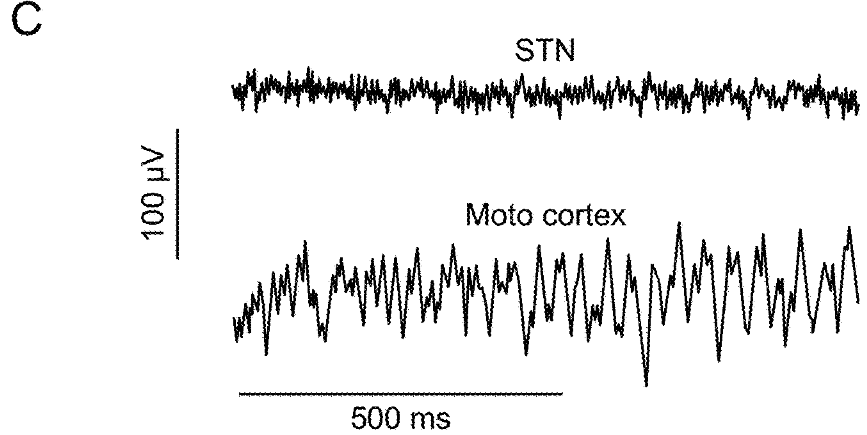
Figure 1:
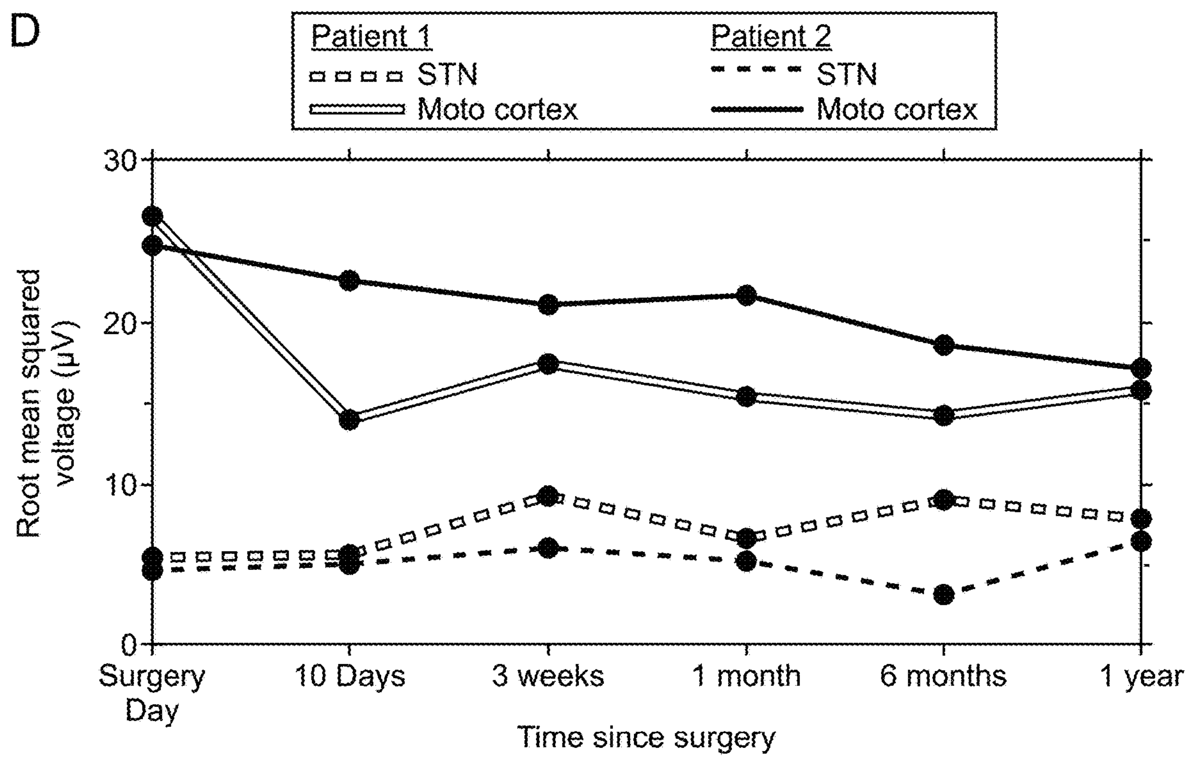

The present disclosure provides methods for detecting hyperkinetic state in a patient having a neurological condition. In certain aspects, the patient may be a human patient who is receiving treatment for the neurological condition. Aspects of the methods include changing a treatment regimen for the neurological condition upon detection of hyperkinetic state in the patient. Also provided are devices, systems, and kits for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "the electrode" includes reference to one or more electrodes, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the present disclosure include methods for detecting hyperkinetic state in a human patient suffering from a neurological condition. An aspect of the methods include measuring oscillatory activity in brain of the patient, where presence of oscillatory activity in the range of 60 Hz-90 Hz, and/or, if during DBS, at half the frequency at which DBS is delivered, marks the presence of hyperkinetic state in the patient.

The terms "hyperkinetic state" or "hyperkinesia" or "hyperkinesis" are used interchangeably herein and refer to state of excessive restlessness, an increase in muscular activity resulting in excessive movements. Hyperkinetic state is a feature of a variety of neurological disorders, including dystonia and Parkinson's disease (PD) in which dyskinesia, involuntarily movements, can occur after prolonged treatment with medications such as levodopa.

The terms "neurological disorder," "movement disorder," "neurological movement disorder" or "neurological condition," as used herein interchangeably and refer to any brain disease, anomaly, or condition causing a subject to have abnormal voluntary and/or involuntary movements, or slow, reduced movements. Exemplary neurological disorders include, but are not limited to, Parkinson's disease, dyskinesia, dystonia, Huntington's disease, Tourette syndrome, essential tremor, anxiety, mood disorders, obsessive compulsive disorders, and chronic pain disorders. These disorders may be associated with hyperkinetic state where the patient suffers from involuntary muscle movements which may be caused by excessive muscle activity or contraction.

The terms "dyskinesias" and "dyskinesia" are used interchangeably herein and refer to a category of movement disorders that are characterized by involuntary muscle movements, including movements similar to tics or chorea. Dyskinesia can vary from a slight movement of the hands to an uncontrollable movement of the upper body or lower extremities. In certain cases, the dyskinesia may be levodopa-induced dyskinesia which correlates to plateau L-DOPA level, such as in Parkinson's disease patients receiving treatment with levodopa. The term "dystonia" refers to another excessive movement disorder which shares state of hyperkinism with dyskineseas such as involuntary muscle contractions that cause slow repetitive movements. Some patients with dystonia suffer from abnormal postures due to prolonged uncontrolled muscle contraction.

Also provided herein are methods for monitoring treatment of a neurological disorder and/or for modulating treatment of a neurological disorder. Aspects of these methods include measuring oscillatory activity in brain of a patient receiving a treatment for the neurological disorder, where presence of oscillatory activity in the range of 60 Hz-90 Hz, and/or, if during DBS, at half the frequency that DBS is delivered, indicates the presence of hyperkinetic state in the patient; and changing the treatment regimen upon detection of oscillatory activity in the range of 60 Hz-90 Hz, and/or, if during DBS, at half the frequency that DBS is delivered.

A neurological movement disorder may be treated using embodiments of methods of the present disclosure. By "treatment," "treatment," or "treat" is meant that at least an amelioration of the symptoms associated with the condition afflicting the subject is achieved, where amelioration is used in a broad sense to refer to at least a reduction in the magnitude of a parameter, e.g., a symptom, associated with the condition being treated. As such, treatment includes a broad spectrum of situations ranging from slowing, delaying, or halting progression of a condition and/or a related symptom, up to and including completely eliminating the condition, along with any associated symptoms. Treatment therefore includes situations where the condition, or at least a symptom associated therewith, is completely inhibited, e.g., prevented from happening, or stopped, e.g., terminated, such that the subject no longer suffers from the condition, or at least the symptoms that characterize the condition. Treatment also includes situations where the progression of the condition, or at least the progression of a symptom associated therewith, is slowed, delayed, or halted. In such cases, a subject might still have residual symptoms associated the pathological condition, but any increase in the severity or magnitude of the symptoms is slowed, delayed, or prevented.

In certain cases, the human patient may be a patient diagnosed with a neurological movement disorder and receiving a treatment for the neurological movement disorder. In certain cases, the treatment may include administration of a medication for treatment of the neurological movement disorder over a prolonged period of time. In other cases, the treatment may include administering deep brain stimulation to the patient. Upon detecting oscillatory activity in the range of 60 Hz-90 Hz, and/or, if during DBS, at half the DBS frequency from the patient's brain, the treatment for the neurological movement disorder may be changed. For example, the dose of the medication may be reduced. The reduction may be immediate, such as, withholding the medication until hyperkinesia is no longer detected. In other embodiments, the reduction may be gradual, such as a reduction is dosage of the medication over a period of time.

In embodiments where the patient is receiving DBS, a parameter of the DBS may be changed. The change in the parameter of the DBS may be maintained for an extended period of time. In certain cases, the hyperkinetic state (e.g., excessive movement associated with dyskinesias or dystonia) may be caused by the treatment such as by the medication or the DBS-thus, changing the treatment may result in treatment of the disorder. Therefore, methods of the present disclosure are useful in improving treatment of movement disorders by detecting hyperkinetic state and changing the treatment to treat the dyskinesias/dystonia. The change in the treatment may be carried out for a period of time sufficient to treat the neurological disorder (e.g., dyskinesias/dystonia), such as, until a reduction or complete disappearance of the oscillatory activity in the 60 Hz-90 Hz, and/or half DBS frequency, is achieved.

In certain embodiments, the oscillatory activity comprises potentials such as, local field potentials (LFPs). The oscillatory activity may be referred to as power or amplitude measured in the region of the brain. In certain cases, measuring the oscillatory activity comprises detecting potentials such as, cortical field potentials. The oscillatory activity may be transmitted by any convenient means to a device, such as a pulse generator or data analyzer, which may include a processor. The device determines whether the detected oscillatory activity includes a peak in the range of 60 Hz-90 Hz (e.g., 60 Hz-85 Hz, or 60 Hz-80 Hz), and/or at half the DBS frequency. If a peak in the 60 Hz-90 Hz range, and/or at half the DBS frequency, is not detected, then the processor outputs a result noting absence of hyperkinetic state or does not take an action changing a treatment parameter. If a peak in the 60 Hz-90 Hz range and/or at half the DBS frequency is detected, then the processor outputs instructions for changing the treatment being administered to the patient or automatically changes the treatment. For example, the patient may be receiving a treatment that includes deep brain stimulation, via a pulse generator. In certain aspects, the pulse generator output is changed prior to administration of the deep brain stimulation to change one or more parameters of the stimulation (e.g., contact choice, amplitude, frequency, and the like) when a peak in the range of 60 Hz-90 Hz, and/or at half the DBS frequency, is detected. In certain cases, the measuring oscillatory activity, detecting a peak in the range of 60 Hz-90 Hz and/or at half the DBS frequency, and changing a parameter of the DBS may be carried out in multiple cycles till a parameter effective for treatment of the hyperkinetic state and the neurological movement disorder is established.

The measuring of the oscillatory activity may be carried out chronically, for example, for a period of 12 hours to 10 years, such as, 1 day, 3 days, 10 days, 30 days, 3 months, 10 months, a year, 3 years, or longer. In certain cases, the measuring of the oscillatory activity may be commenced after the patient has been receiving medication to treat the neurological movement disorder for a period of time, such as, after 3 days, a week, a month or longer. In certain cases, the treatment for neurological movement disorder of the patient may include DBS and the measuring of the oscillatory activity may be commenced with the DBS or shortly after the DBS, such as, within seconds, minutes, or hours after the DBS.

In certain aspects, brain activity is measured at a surface of the brain, subdural space over the surface of the brain or in a region of the brain. For example, the oscillatory activity may be measured in or near motor cortex, primary motor cortex, subthalamic nucleus (e.g., dorsal or ventral STN), thalamus, basal ganglia, nuclei from basal ganglia thalamo cortical loop, striatum, globus pallidus (GP), and/or any region connected to the STN and motor cortex. The oscillatory activity may be recorded using a lead, bipolar contact pair, or electrode placed over a region of the brain and/or implanted into the brain. In certain cases, the oscillatory activity indicative of hyperkinetic state associated with a neurological disorder (e.g., dyskinesias or dystonias, etc.), as recorded in or near a region of the brain may be 60 Hz-90 Hz, 60 Hz-80 Hz, 60 Hz-85 Hz, 65 Hz-80 Hz, 70 Hz-78 Hz, 70 Hz-75 Hz, 75 Hz-78 Hz, or 75 Hz-80 Hz, e.g., about 60 Hz, 65 Hz, 70 Hz, 75 Hz, or 80 Hz.

In certain cases, the oscillatory activity (e.g., field potentials) may be recorded from a bipolar contact pair placed in or over the patient's brain (e.g., primary motor cortex and/or the STN). The bipolar contact pair may be non-penetrating electrodes, as shall be described more fully below. Further, the location of the contacts may vary. In some embodiments, at least one electrode may be located in the subdural space over the primary motor cortex M1. In certain embodiments, a deep brain electrode may be used to record the oscillatory activity. In certain embodiments, a deep brain stimulation electrode may be used to stimulate a region of the patient's brain, such as the thalamus, subthalamic nucleus, and/or basal ganglia. In certain embodiments, a deep brain electrode may be used to stimulate a region(s) of the brain and to record oscillatory activity from the region(s).

In certain aspects, methods of the present disclosure may utilize one or more commercially available electrodes, devices, or systems. Methods of performing deep brain stimulation, and deep brain stimulation devices and/or systems of interest include, but are not limited to, those methods, devices, and/or systems described in U.S. Pat. Nos. 5,716,377; 5,843,148; 6,066,163; 6,253,109; 6,463,328; 6,484,059; 6,539,263; 6,587,724; 6,484,059; 6,920,359; 7,003,352; 7,033,326; 7,149,574; 7,151,961; 7,212,867; 7,295,880; 7,295,880; 7,346,382; 7,369,899; 7,539,543; 7,809,446; 7,904,134; and 7,957,808; the disclosures of which are each incorporated herein by reference.

Various aspects of embodiments of the methods shall now be described in greater detail below.

Recording Oscillatory Activity

Aspects of embodiments of the subject methods involve recording oscillatory activity such as field potentials from a region of the patient's brain. According to certain embodiments, recording field potentials (e.g., cortical field potentials) is carried out by electrocorticography (ECoG) or electroencephalography (EEG). In certain aspects, recording field potentials involve the use of an array (e.g., an electrocorticography array, such as a multi-contact electrocorticography strip). The recording element may be a strip, such as a subdural electrocorticography strip. The recording element may include a non-brain-penetrating electrode (e.g., an ECoG or EEG electrode), and in certain aspects may include only non-brain-penetrating electrodes.

The precise number of contacts (e.g., electrodes) contained in a strip may vary. In certain aspects, an electrocorticography strip may include one or more contacts, such as 2 or more, including 3 or more, e.g., about 3 to 6 contacts, about 6 to 12 contacts, about 12 to 18 contacts, about 18 to 24 contacts, about 24 to 30 contacts, about 30 to 48 contacts, about 48 to 72 contacts, about 72 to 96 contacts, or about 96 or more contacts. Where the array includes more than one contact, the contacts may be arranged into a regular repeating pattern (e.g., a grid, such as a grid with about 1 cm spacing between contacts), or no pattern. The contacts may be made of any convenient material for recording field potentials. In certain aspects, when EEG is used to measure the field potentials, the EEG electrodes may be held to the scalp with a cap.

The size of each contact may also vary depending upon such factors as the number of contacts in the strip, the location of the contact, the material, the neurological movement disorder, the age of the patient, and other factors. In certain aspects, a contact has a size (e.g., a diameter) of about 5 cm or less, 4 cm or less, 3 cm or less, 2 cm or less, 1 cm or less, 0.5 cm or less, 0.1 cm or less, 5 mm or less, such as about 4 mm or less, including about 3 mm, about 2 mm, about 1 mm, about 0.5 mm, or about 0.25 mm.

In certain embodiments, at least one contact is placed on the surface of a subject's brain so as to be placed in or on the primary motor cortex (M1). In certain aspects, one or more contacts are placed in or on M1, such as 2 or more, including 3 or more, e.g., about 3 to 5 contacts, about 5 to 8 contacts, or about 8 to 12 contacts. To facilitate placement of the at least one contact in a location, in certain aspects one or more markers (e.g., a radio-opaque marker) may be used. For instance, in certain aspects a marker, such as a radio-opaque marker, may be placed on the scalp over a desired location, such as the subdural space over M1. A hole, such as a burr hole, may be made in the subject's skull using any convenient means known in the art. In other aspects, a burr hole may already be present. For instance, a hole may already be present if already formed for deep brain stimulation lead placement. The hole may be used to advance the contact(s) to the desired location.

In certain aspects, an additional step may be performed to identify which contact(s) are closest to a desired location, such as M1. For example, contacts closest to M1 may be determined by anatomical and/or physiological methods, such as intraoperative CT merged to the preoperative MRI, allowing for the visualization of the contacts, or lateral fluoroscopy on which the radio-opaque marker placed over M1 could be visualized. In other aspects, the closest contact to a location, such as M1, may also, or instead, be identified using nerve stimulation. For instance, the median nerve may be stimulated in order to generate a somatosensory evoked potential (e.g., frequency=2 Hz, pulse width=200 μsec, pulse train length=160, amplitude 25-40 mAmp), with the closest electrode to M1 identified as the most posterior contact showing a negative N20 waveform.

Once contacts are placed, the field potentials may be recorded using any convenient means known in the art. In certain aspects, field potentials may be recorded using a recording system, such as a Guideline 4000 system (FHC Inc, Bowdoin, ME) or an Alpha Omega Microguide Pro (Alpha Omega, Inc, Nazareth, Israel), and/or biosignal amplifiers, such as Synamps2 biosignal amplifiers (Neuroscan, El Paso, TX), or Activa® PC+S or ActiveTwo system (Biosemi).

Recorded field potentials may be processed. Such processing may include applying one or more filters, such as a bandpass filter and/or a notch filter. Further, the sampling rate of the field potentials may be altered.

For example, in certain aspects processing may include applying a bandpass filter. A bandpass filter may separate the raw field potentials data in about 2 to about 100 different frequency bands, or more. In certain embodiments, a bandpass filter may split a signal into about 2 frequency bands, about 4 frequency bands, about 6 frequency bands, about 8 frequency bands, about 10 frequency bands, about 12 frequency bands, about 14 frequency bands, about 16 frequency bands, about 25 frequency bands, about 40 frequency bands, about 55 frequency bands, about 70 frequency bands, about 75 frequency bands, about 85 frequency bands, about 95 frequency bands, about 150 frequency bands, or more. Specific frequency bands may be selected to divide field potentials data into physiologically important ranges. In some embodiments, a bandpass filter is employed to produce a signal including mu frequencies, beta frequencies, gamma frequencies, high gamma frequencies, or other ranges known to correspond to particular brain wave frequencies.

In certain aspects, one or more notch filters may be applied to the field potentials to remove electrical hum or other noise, such as that from an A/C current. According to certain embodiments, independent component analysis may be used to remove artifacts caused by electrical hum, other noise, or artifact from the DBS stimulation. Independent component analysis can implemented using the EEGLAB toolbox. In certain aspects, the sampling rate of field potentials may be altered using any convenient means, such as digitally. For instance, field potentials may be digitized at a sampling rate of about 200 samples per second or more, such as about 400 to 10000 samples per second, including about 400 to 2000 samples per second, about 400 to 1500 samples per second, or about 1000 samples per second. In certain embodiments, the field potentials may be local field potentials (LFPs).

Deep Brain Stimulation

Aspects of embodiments of the present disclosure include administration of deep brain stimulation. As described above, deep brain stimulation has been widely used and is well known in the art. Any convenient means of administering deep brain stimulation may be employed in practicing the subject methods.

In certain aspects, methods of the present disclosure involve placing one or more deep brain stimulation electrodes. Such surgical placement may be performed using any of a variety of methods known in the art, such as the approaches described in Starr P A, et al. (2002) *Journal of Neurosurgery* 97:370-387 and Ostrem J L, et al. (2011) *Neurology* 76:870-878; the disclosures of which are incorporated herein by reference. For example, an intended target location in the brain of a human patient diagnosed with a nerological movement disorder, such as a STN target location, may be identified as a T2 hypointensity immediately lateral to the anterior margin of the red nucleus and superior to the lateral part of the substantianigra pars *reticulata* (generally close to 12 mm lateral, 3 mm posterior, and 4 mm inferior to AC-PC). Final adjustments on target coordinates may be made during the surgery based on identification of movement-related single cell discharge. A DBS lead (such as a Activa® SC, Activa® PC+S, or model 3389, Medtronic, Inc., Minneapolis, Minnesota, USA) may be placed at these coordinates with the most ventral contact (contact 0) at the base of STN and contact 1 in the center of the motor territory of the STN. Targeting may be confirmed by evaluation of stimulation induced symptom improvement and adverse effects, as well as by visualization of DBS lead location on an intraoperative CT scan as described in Shahlaie K, et al. (2011) *Neurosurgery* 68:114-124; the disclosure of which is incorporated herein by reference. An additional postoperative MRI may be used to confirm the correct placement of DBS leads in each patient (see, e.g., FIG. 2).

As noted in the preceding sections, the DBS may be used for treating a neurological movement disorder. The DBS treatment may cause a side-effect that includes dyskinesias. Upon detection of dyskinesias, the DBS treatment may be changed to reduce the dyskinesias. As noted herein, the neurological movement disorder may be Parkinson's disease, essential tremor, dystonia, and treatment-resistant obsessive-compulsive disorder, etc.

Administration of a Pharmacological Agent

In certain cases, the human subject diagnosed with a neurological movement disorder may be undergoing treatment by administration of an effective amount of at least one pharmacological agent. By "effective amount" is meant a dosage sufficient to prevent or treat a neurological movement disorder in a subject as desired. The effective amount will vary somewhat from subject to subject, and may depend upon factors such as the age and physical condition of the subject, severity of the neurological movement disorder being treated, the duration of the treatment, the nature of any concurrent treatment, the form of the agent, the pharmaceutically acceptable carrier used if any, the route and method of delivery, and analogous factors within the knowledge and expertise of those skilled in the art. Appropriate dosages may be determined in accordance with routine pharmacological procedures known to those skilled in the art, as described in greater detail below.

If a pharmacological approach is employed in the treatment of a neurological movement disorder, the specific nature and dosing schedule of the agent (i.e., medication regimen) will vary depending on the particular nature of the disorder to be treated. Representative pharmacological agents that may find use in certain embodiments of the subject invention include, but are not limited to, levodopa, carbidopa, catechol O-methyltransferase inibitors, monoamine oxidase inhibitors, dopamine agonists, anticholinergics, catecholamines, baclofen, benzodiasepines, tetrabenezine, diazepam, clonazepam, lorazepam, and the like.

In certain aspects, the administration of a pharmacological agent involves using a pharmacological delivery device such as, but not limited to, pumps (implantable or external devices), depots, epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags.

As noted herein, the medication may have a side effect that includes dyskinesias. Upon detection of dyskinesias using the methods disclosed herein, the medication may be withheld or decreased or replaced with a different medication.

In certain cases, the patient may have an excessive movement disorder such as dystonia. Upon detection of oscillatory activity indicative of hyperkinetic state associated with disorders (e.g., PD, dyskinesias or dystonias, etc.), as recorded in or near a region of the brain such as primary motor cortex, subdural space over the primary motor cortex, STN (e.g., dorsal or ventral STN), e.g., oscillatory activity in the range 60 Hz-90 Hz, 60 Hz-80 Hz, 60 Hz-85 Hz, 65 Hz-80 Hz, 70 Hz-78 Hz, 70 Hz-75 Hz, 75 Hz-78 Hz, or 75 Hz-80 Hz, e.g., about 60 Hz, 65 Hz, 70 Hz, 75 Hz, or 80 Hz, the patient may be given a different treatment regimen. For example, the patient's dystonia may be treated by changing the medication regimen, e.g., using a different drug, or a different dosage or different dosing schedule of the medication.

Changing Parameters of Administration of Deep Brain Stimulation

In certain embodiments of the subject methods, if the measured oscillatory activity is in the range of 60 Hz-90 Hz, or at half the DBS frequency, one or more parameters of a deep brain stimulation and/or administration of a pharmacological agent may be changed. Accordingly, the subject methods may be performed using suitable computing means such as suitable hardware/software for performing the subject methods.

In certain embodiments, programming may control a device to administer a deep brain stimulation and/or a pharmacological agent to a subject, e.g., programming may be configured to determine suitable amplitude, frequency, intensity, dosage, electrode configuration, etc. In certain embodiments programming may control a device to administer deep brain stimulation to a subject, e.g., may control the activation/termination of a pulse generator device including selecting suitable parameters. Such programming may be configured to, or otherwise be capable of, directing a microprocessor to activate, i.e., turn "on" and "off" a deep brain stimulation applying device for applying deep brain stimulation to a subject. For example, if so determined, the processor may direct the deep brain stimulation applying device to provide the appropriate deep brain stimulation to result in the desired action.

Accordingly, a processor may select the appropriate parameters (e.g., frequency, intensity, duration, electrode configuration etc.) depending on what is required and direct a deep brain stimulation applying device and/or a drug delivery device to implement the parameters.

Thus in certain aspects, the subject methods operate as a closed-loop control system which may automatically adjust one or more parameters in response to presence of a peak in 60 Hz-90 Hz, and/or half DBS frequency range in a cortical or STN region in the patient. Under a closed-loop feedback system to provide automatic adjustment of parameters an improved therapy is provided.

Improved Therapy

The detection of the activity in 60 Hz-90 Hz range, and/or half the DBS frequency, in the patient indicative of hyperkinesia implies that oscillatory activity in this range can be used as a control signal for "close-loop" devices. Such "smart" devices may record brain (e.g., cortical) activity and upon detection of hyperkinetic state determine computationally how to use DBS to minimize hyperkinetic state or how to change medication dosage to minimize hyperkinetic state. The closed-loop device may be a closed-loop DBS device or a closed loop activity detection and medication administration device.

Devices

As described above, the present disclosure also provides devices for practicing the subject methods. Devices of the present disclosure may be employed to carry out one or any combination of steps of the methods of the present disclosure according to any embodiment as described above in the section entitled "Methods", which description is incorporated herein. According to certain embodiments, the devices include a computer-readable medium having instructions for carrying out any aspect of the methods of the present disclosure. The instructions may be executed by a processor. In certain aspects, devices of the present disclosure include an input configured to receive oscillatory activity such cortical or subcortical field potentials from at least one electrode placed in an appropriate location in the brain of the human subject; an output configured to be in electronic communication with a pulse generator for administering deep brain stimulation or a device for administering a medication to the patient or a monitor or speaker for outputting a message to adjust the medication; a processor in electronic communication with the input and the output, the processor programmed to: detect presence of an oscillatory activity ranging from 60 Hz-90 Hz, and/or half the DBS frequency; and change at least one parameter of the pulse generator or change the medication dosage or output a message to a user to change the medication dosage. Such input(s) and/or output(s) may include standard connections known in the art.

The processor may be programmed to perform a subject method, and thus may be programmed to change one or more parameters of treatment of the human patient upon detecting hyperkinetic state by measuring oscillatory activity of about 60 Hz-90 Hz, or half the DBS frequency, in the patient, and the like, as described above.

A great many variations of the subject devices may be employed. For example, in certain aspects a subject device includes a display, such as an LCD display, e-ink display, and the like. The display may include a user interface (e.g., a graphical user interface) that is in communication with the processor. The user interface may be used to set one or more parameters by a user who may be the patient, a doctor, nurse, or other caregiver. For example, the user interface may be used to set initial parameters for the pulse generator, to display instructions to change a treatment parameter such as medication dosage or a parameter of DBS, to display message noting that a treatment parameter has been changed in response to detection of oscillatory activity of about 60 Hz-90 Hz, or half the DBS frequency in the patient, and the like.

In certain aspects, the device may require a user intervention before taking one or more actions. For example, in certain embodiments the processor is programmed to require a user intervention via the user interface before changing at least one parameter of the treatment such as a parameter of a pulse generator or a pump for delivering medication. The user intervention may be made via any convenient means, such as by the user interface of the device. In other aspects, the device may automatically change a treatment parameter upon detection of oscillatory activity of about 60 Hz-90 Hz, or half the DBS frequency, in the patient.

Aspects of embodiments of subject devices include a data logging element. The data logging element is in communication with the processor, and configured to non-transiently record at least the oscillatory activity and the at least one parameter of a pulse generator. The data logging element may, in certain aspects, further record other parameters.

In certain aspects, a device may include an output that is configured to be in electronic communication with a drug delivery device configured to administer a pharmacological agent to a subject. In such devices, the processor may be programmed to change at least one parameter of the drug delivery device based on detection of oscillatory activity of about 60 Hz-90 Hz, and/or half the DBS frequency, in the patient. The specific type of drug delivery device may itself vary, with pharmacological delivery devices of interest including, but not limited to, pumps (implantable or external devices), epidural injectors, syringes or other injection apparatus, catheter and/or reservoir operatively associated with a catheter, etc.

Devices may be configured to operate as a closed-loop device which may automatically adjust one or more parameters in response to detection of oscillatory activity of about 60 Hz-90 Hz, and/or half the DBS frequency, in the patient. For the closed-loop feedback device to provide automatic adjustment of parameters, a sensor (e.g., one or more electrodes, such as one or more ECoG or EEG electrodes) that measures oscillatory activity may be utilized. More detailed descriptions of devices and systems that may be employed in the practice of the present disclosure, and other examples of devices and feedback control techniques that may be employed are disclosed in U.S. Pat. No. 5,716,377, which is incorporated herein by reference.

Systems

Also provided by the present disclosure are systems for detecting hyperkinetic state in a patient having a neurological disorder and for treating the neurological disorder. Systems of the present disclosure may be employed to carry out one or any combination of steps of the methods of the present disclosure according to any embodiment as described above in the section entitled "Methods", which description is incorporated herein. According to certain embodiments, the systems include a computer-readable medium having instructions for carrying out any aspect of the methods of the present disclosure. The instructions may be executed by a processor. In certain aspects, systems include an electrode (e.g., a subdural electrode) adapted to record oscillatory activity (e.g., field potentials) from the primary motor cortex and/or STN of the patient; a data analyzer in electronic communication with the electrode and a pulse generator, the data analyzer comprising: a processor programmed to determine presence of oscillatory activity in the 65 Hz-90 Hz range, and/or half the DBS frequency; and change a parameter of deep brain stimulation of the patient via the pulse generator.

Accordingly, in certain aspects systems of the present disclosure may be computer-based systems. A "computer-based system" refers to the hardware, software, and data storage devices used to analyze the information of the present invention. The minimum hardware of embodiments of the computer-based systems includes a central processing unit (CPU) (e.g., a processor), an input device, an output device, and a memory. Any one of the currently available computer-based systems may be suitable for use in the embodiments disclosed herein. The data storage device may include any manufacture including a recording of the present information as described above, or a memory access means that can access such a manufacture. For example, embodiments of the subject systems may include the following components: (a) a communications module for facilitating information transfer between the system and one or more users, e.g., via a user computer or workstation; and (b) a processing module for performing analysis of recorded oscillatory activity.

Systems may be configured to operate as a closed-loop system which may automatically adjust one or more parameters in response to detection of oscillatory activity in the 60 Hz-80 Hz range, and/or half the DBS frequency in the patient. For the closed-loop feedback system to provide automatic adjustment of parameters, a sensor (e.g., one or more electrodes, such as one or more ECoG or EEG electrodes) that record oscillatory activity from the brain (e.g., cortex or STN) may be utilized. More detailed descriptions of systems and devices that may be employed in the practice of the present disclosure, and other examples of systems and feedback control techniques that may be employed are disclosed in U.S. Pat. No. 5,716,377, which is incorporated herein by reference.

Embodiments of systems of the present disclosure include a drug delivery device, such as described above, in electronic communication with the processor and configured to administer a pharmacological agent to a subject. In such systems, the processor is further programmed to change a dosage regimen of the pharmacological agent to the subject via the drug delivery device if oscillatory activity in the 60 Hz-90 Hz range, and/or half the DBS frequency, is detected in the patient.

Additionally, systems of the present disclosure may include a number of additional components, such as data output devices, e.g., monitors, printers, and/or speakers, data input devices, e.g., interface ports, a keyboard, a mouse, etc., fluid handling components, power sources, etc.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a deep brain stimulation and/or a pharmacological agent to a subject, e.g., programming may be configured to determine suitable amplitude, frequency, electrode configuration, intensity, dosage, etc. In certain embodiments programming may control a device to administer deep brain stimulation to a subject, e.g., may control the activation/termination of a pulse generator device including selecting suitable parameters. Programming may be configured to, or otherwise be capable of, directing a microprocessor to activate, i.e., turn "on" and "off" a deep brain stimulation applying device for applying deep brain stimulation to a subject. For example, if so determined, the processor may direct the deep brain stimulation applying device to provide the appropriate deep brain stimulation to result in the desired action. Accordingly, a processor may select the appropriate parameters (e.g., frequency, intensity, electrode configuration, duration, dosage, etc.) depending on what is required and direct a deep brain stimulation applying device and/or a drug delivery device to implement the parameters.

Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits

Also provided are kits for practicing the subject methods. Kits may include one or more devices or systems, as described above, and/or pharmacological agents, as described above.

The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as described above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I.V. bag and tubing, electrodes for placement in desired region of the brain, etc.

The subject kits may also include a deep brain stimulation applying device, as described above. The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. flash drive, CD-ROM or DVD-ROM, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

Utility

The subject methods, devices, systems and kits find use in a variety of applications in which it is desired to detect hyperkinesia and/or treat a subject for a condition, e.g., a neurological movement disorder; to reduce the abnormal motor signs of a condition (e.g., clinical disability associated with a movement disorder). Specific neurological disorders of interest include, but are not limited to, Parkinson's disease, and primary and secondary dystonias, dyskinesia, Huntington's disease, essential tremor, Tourette syndrome, mood disorders, psychotic disorders, and other psychiatric conditions.

In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. Moreover, suitable subjects include those who have and those who have not been diagnosed with a neurological movement disorder. In certain embodiments, the subject methods may include a diagnostic step. Individuals may be diagnosed as being in need of the subject methods using any convenient protocol suitable for use in diagnosing the presence of a neurological movement disorder, such as visual diagnosis, physical testing, neurological exam, blood and/or urine testing, electrical recording (e.g., electromyography or electroencephalography), genetic testing, imaging (e.g., CT scan, MRI scan, and/or PET scan), and the like. In addition, individuals may be known to be in need of the subject methods, e.g., they are exhibiting one or more clinical presentations of a neurological movement disorder.

Methods of determining the neurological state of a subject are known to those of skill in the art (such as by using diagnosis protocols, e.g., as described above). A subject's neurological state may be understood to refer to the presence or absence of one or more neurological movement disorders, e.g. the presence of midstage PD that is no longer optimally improved by medication, and/or the presence of clinical presentations of a neurological movement disorders. Accordingly, the phrase "maintaining the neurological state" of a subject refers to the preservation or the subject's existing state (e.g., the subject does not develop one or more new neurological movement disorders if the subject does not already have the condition; the subject does not start to exhibit new clinical presentations of a neurological movement disorder; etc.).

Methods of the present disclosure may further include assessing the efficacy of a treatment protocol, which may be performed using any convenient protocol, e.g., by monitoring the rate of improvement of a neurological movement disorder (such as by using the diagnosis protocols, e.g., as described above).

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Example 1

Network oscillations might also play a role in the adverse effects caused by PD therapies. One such effect is dyskinesia. Dyskinesia is characterized by involuntary choreiform movements associated with dopaminergic medication and/or deep brain stimulation (DBS) (Bastide et al., 2015, Prog Neurobiol 132:96-168). These movements may preclude optimal therapeutic benefit from medication or DBS. Local field potential (LFP) recordings from cortex and basal ganglia in a rodent model of parkinsonism have shown that levodopa-induced dyskinesias are associated with an increase in gamma oscillatory power in both structures (Halje et al., 2012, J Neurosci 32:16541-16551). Network changes associated with dyskinesia have not been established in humans.

Invasive human data have been obtained mainly from the basal ganglia, through temporarily externalized leads in the early postoperative period (Brown and Williams, 2005; Kuhn et al., 2006; Hammond et al., 2007; Kuhn et al., 2008). Narrowband gamma oscillations have been reported in human basal ganglia recordings, but the relationship to dyskinesia and the consistency of the effect are not clear (Cassidy et al., 2002, Brain 125:1235-1246; Williams et al., 2002, Brain 125:1558-1569; Alonso-Frech et al., 2006, Brain 129:1748-1757; Alegre et al., 2012, Mov Disord 27:1178-1181; Weinberger et al., 2012, Clin Neurophysiol 123:358-368; Cagnan et al., 2014, Clin Neurophysiol 125: 777-785). Timing and duration of dyskinesia can be unpredictable, and they are often reduced immediately following DBS surgery, limiting the utility of short-term recording strategies.

To circumvent these shortcomings, we have utilized a totally implantable bidirectional neural interface in humans requiring DBS implantation for the treatment of motor fluctuations and medication-induced dyskinesia. This investigational device, Activa PC+S (Medtronic Inc.) has the same stimulating capabilities as standard DBS devices, but also allows long-term recording and storage of electrocorticography (ECoG) potentials and LFPs. With the view that abnormal movement in PD arises from cortical-basal ganglia interactions (Silberstein et al., 2005, Brain 128:1277-1291; de Hemptinne et al., 2013, Proc Natl Acad Sci USA 110: 4780-4785; de Hemptinne et al., 2015, supra), we simultaneously recorded potentials from a permanently implanted, 4-contact ECoG strip placed over motor cortex, as well as from the therapeutic subthalamic nucleus (STN) 4-contact lead. We focused our analysis on data from 2 patients collected over 12 months. We show that dyskinesia is associated with the emergence of a narrowband gamma oscillation throughout the basal ganglia-thalamo-cortical motor loop, which is modulated by DBS. This oscillatory activity suggests new strategies for feedback-controlled DBS that could limit hyperkinetic adverse effects.

Materials and Methods

Consent, Regulatory Approvals, and Patient Selection

This protocol was approved by the UCSF institutional review board (protocol #13-10878) under a physician sponsored investigational device exemption (IDE # G120283). The study was registered at Clinical Trials.gov (NCT01934296). Informed consent was obtained under the Declaration of the Principles of Helsinki. During this study, five patients with PD (2 female, 3 male) were implanted with Activa PC+S, but only two patients (1 female, 1 male) had a large number of recordings with and without dyskinesia, both on and off medication and on and off DBS, as well as favorable signal to noise ratios at gamma band frequencies. Therefore the statistical analysis of grouped data is restricted to these two patients. A much smaller data set is available from two additional patients, so for these, only individual examples are shown. One of these patients had only rare dyskinesia after DBS implantation, and the other had a low signal-to-noise ratio for cortical recordings such that frequencies>70 Hz were near or below the noise floor of the device and not reliably detected. The final patient did not experience dyskinesia post-implantation, so no data from that subject were included. Baseline characteristics of the two patients included in the statistical analysis, as well as the two additional patients for whom we present example data, are provided in Table 1.

TABLE 1

Baseline characteristics of study patients.

| Patent # | Gender | Age (years) | Disease Duration (years) | ECoG/ LFP Side | Baseline UPDRS III Score (on/off) | MOCA Score | BDI Score |
|---|---|---|---|---|---|---|---|
| 1 | F | 47 | 15 | L | 16/68 | 28 | 14 |
| 2 | F | 59 | 7 | L | 14/29 | 30 | 12 |
| 3* | M | 62 | 8 | R | 30/14 | 28 | 0 |
| 4* | M | 60 | 14 | R | 44/31 | 29 | 11 |

Figure 10:
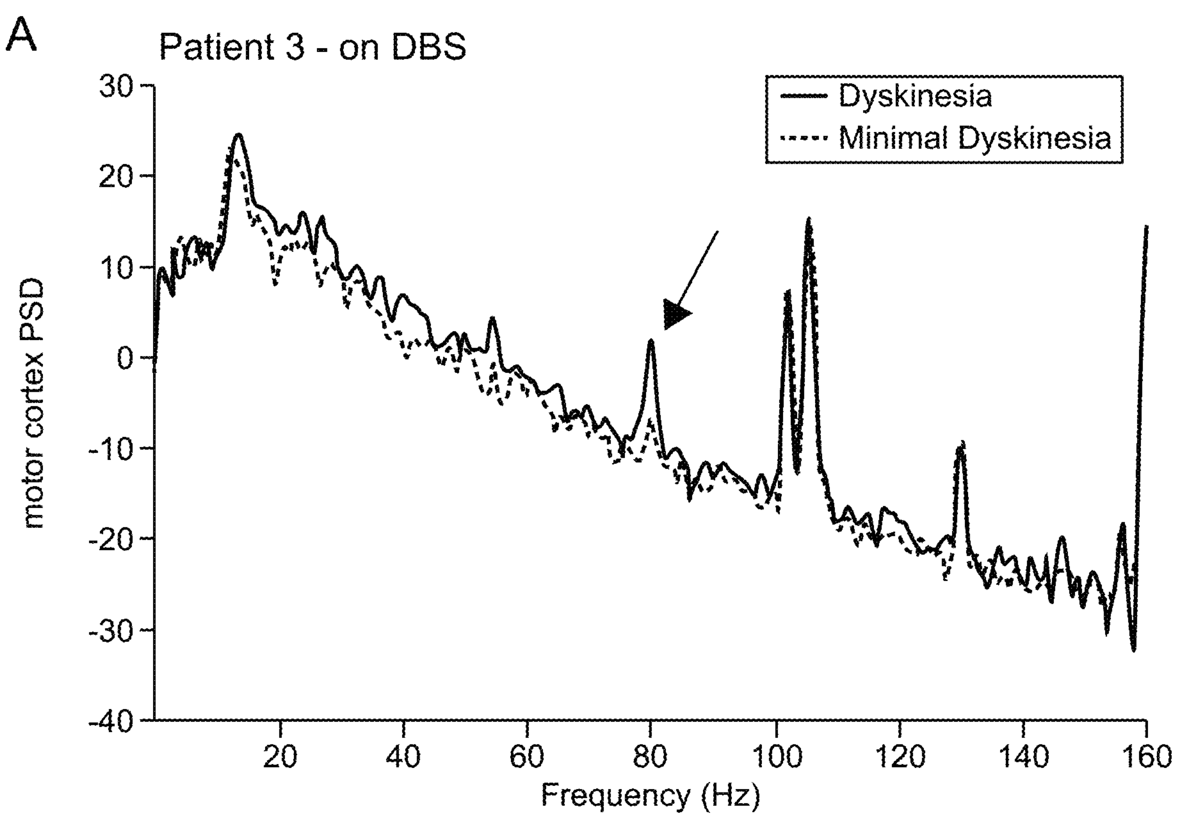
FIG. 10, Panels A-B provide example recordings from patients not included in the grouped statistical analysis.
Figure 10:
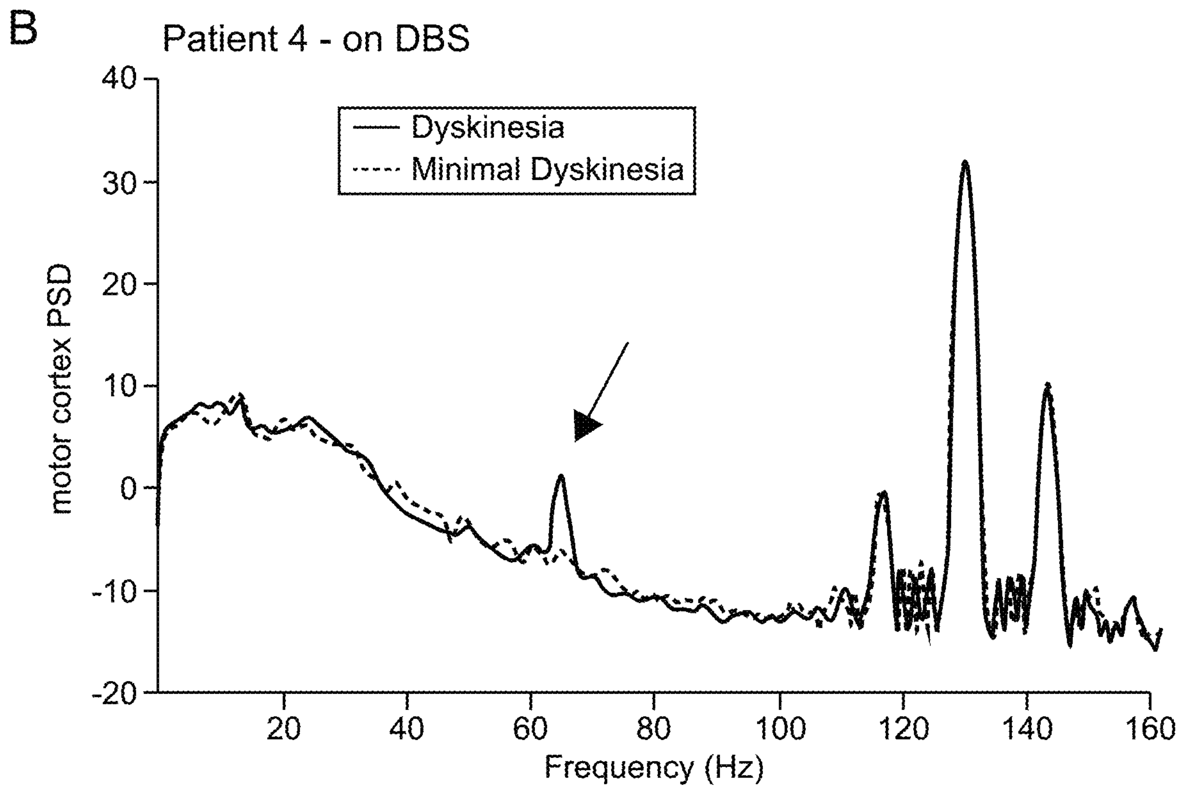

MOCA = Montreal Cognitive Assessment,
BDI = Beck Depression Inventory.
*Data from these patients appear only in FIG. 10.

Clinical Characterization

Study patients were evaluated by a movement disorders neurologist and met criteria for a diagnosis of PD (i.e. presence of bradykinesia and at least one other parkinsonian cardinal sign and responsiveness to levodopa). Baseline motor function in the on and off medication states were characterized using the Unified Parkinson's Disease Rating Scale, motor subscale (UPDRS III). Patients were evaluated by a neuropsychologist to exclude significant cognitive impairment or untreated mood disorder.

Surgery

A quadripolar subthalamic lead (Medtronic model 3389) was placed using frame-based stereotaxy and confirmed by microelectrode recording in the awake state using standard methods (Starr et al., 2002, Journal of neurosurgery 97:370-387). Proper location in the motor territory of the STN was verified by eliciting movement-related single-cell discharge patterns (Starr et al., supra). A quadripolar cortical ECoG lead was placed in the subdural space through the same burr hole used for the subthalamic lead. For patient 1, we used a cylindrical lead (Medtronic model 3391) with 3 mm contact length and 4 mm inter-contact spacing; for all other patients we used a flat lead (Medtronic model 3587A25), with 4 mm contact diameter and 10 mm inter-contact spacing. At least one contact covered the posterior precentral gyms (presumed primary motor cortex), approximately 3 cm from the midline on the medial aspect of the hand knob (Yousry et al., 1997, Brain 120 (Pt 1):141-157). Adequate localization of the ECoG strip was confirmed using intraoperative CT merged to the patient's preoperative MRI, as previously described (Shahlaie et al., 2011, Neurosurgery 68:114-124). Functional localization of the ECoG strip was verified with somatosensory-evoked potentials, as has been previously reported (Crowell et al., 2012, Brain, February; 135(Pt 2):615-30). If time permitted, a movement task described previously (de Hemptinne et al., 2015, supra) was also performed to ensure that canonical movement-related beta decreases and broadband gamma increases were produced (Crone et al., 1998a, Brain 121 (Pt 12):2301-2315; Crone et al., 1998b, Brain 121 (Pt 12):2271-2299). The exiting wire from the cortical contact array was secured to the skull with a titanium miniplate. The free ends of the cortical and subthalamic leads were coiled under the ipsilateral parietal scalp.

The remaining hardware was placed under general anesthesia. In the posterior parietal area, the free ends of the cortical and subthalamic leads were connected to 40 cm lead extenders (Medtronic model 37087), which were tunneled down the neck to a Medtronic Activa PC+S placed in a pocket over the pectoralis muscle (FIG. 1A). The Activa PC+S is identical in shape and size to the standard Activa PC. For all patients except patient 2, a contralateral STN electrode was implanted and attached to a separate Activa SC pulse generator, for clinical purposes only, so that bilateral therapy could be delivered. Patient 2 only received unilateral therapy, as clinically indicated.

FIG. 1. Electrode locations, raw signals, and signal stability over time. A. Schematic of Activa PC+S. B. Electrode locations for patients 1 and 2 over cortex (top) and in STN (bottom). Locations are derived from pre-operative MRI merged to intra-operative CT. C. Raw signals from STN and Motor cortex. D. Root mean square voltage off DBS for motor cortex ECoG potentials and STN LFP, for each patient, recorded over 12 months. Signals are relatively stable over time.

Experimental Design

Following surgery, each patient participated in research visits at regular intervals during which ECoG potentials and STN LFPs were recorded and downloaded wirelessly. These visits included recordings on and off medication in the month prior to initial DBS programming, followed by visits on and off of therapeutic DBS. One month after implantation programming of the STN lead(s) was performed to achieve the best clinical result. The cortical lead was not used for stimulation.

During formal study visits, STN and cortical field potentials were recorded at rest, during an iPad reaching task that has been previously described (de Hemptinne et al., 2015, supra), and during walking. Rest and walking recordings were one to two minutes long, and iPad reaching task recordings were 3-5 minutes long. Some additional brain recordings were initiated in our clinic to document specific phenomena, such as briefly shifting DBS frequency during an episode of dyskinesia to document a shift in the gamma peak frequency (described in Results).

Patients were also given a home data-collection triggering device (Intercept Patient Programmer, model 37441), allowing the patient to initiate brain recordings at home, for a pre-specified duration (1 minute). Patients were instructed to initiate such recordings if they were experiencing dyskinesia, particularly severe 'off' periods, or if they were feeling especially asymptomatic. They were also instructed to take notes on how they felt during each recording, detailing any notable symptoms.

Recordings

Investigator-initiated recordings were activated via the Sensing Programmer Model (8181) and Sensing Programmer Software Model (8180), which are part of the Medtronic Activa PC+S system. The Activa PC+S device allows a maximum of two time domain channels (one from each lead) to be recorded simultaneously. Thus, we typically recorded from one bipolar contact pair in motor cortex and one from STN, with a sampling rate of 800 Hz, unless otherwise specified. To capture data as rapidly as possible from multiple cortical electrodes, we occasionally performed brief "montage recordings", during which the device sampled data from each cortical electrode pair sequentially. Data from each electrode pair were recorded for 30 seconds, before proceeding to the next pair. For these recordings a sampling rate of 422 Hz was used.

The cortical contact pair used for recordings was selected based on which pair showed the clearest somatosensory evoked potential, the strongest movement-related broadband gamma response, and/or strongest beta peak at rest, at the time of initial surgical insertion. Typically, there was good overlap for these three measures in terms of identifying one or two contact pairs. When ambiguity remained, the preoperative Mill merged to the postoperative CT was used to help select an optimal motor cortex contact pair. Additional contacts were sometimes used, particularly if more than one contact pair had shown strong movement-related signals as described above.

The selection criteria for the STN recording configuration differed before and after therapeutic DBS was activated at one month post-implantation, since optimal recording contact pairs depended on which contacts were used for stimulation (stimulation and recording could not be performed from the same contact(s) simultaneously). Stimulation contacts were not known prior to patient's initial DBS programming. Prior to stimulation, recording contacts were based on which contact pair had the largest beta peak the day after surgery (off PD medications). If selection was ambiguous the center contacts (1-2) were used. After stimulation, recording contacts bordering stimulation contacts on either side were used to minimize artifact. Occasionally, no STN contacts were recorded either because an unusually long cortical recording was desired, or more recordings than usual were performed, precluding recording from two sites due to the limited Activa PC+S memory storage capacity Activa PC+S has several built in filters. We avoided filters when possible, so our initial recordings used minimal filters (0.5 Hz high pass filter and a built in 260 Hz anti-aliasing filter), and maximum gain (2000). However, after our early patient initiated therapeutic stimulation, we realized saturation of the amplifier was sometimes occurring, so we began using a 100 Hz low pass filter, and, in cases of especially large stimulation artifact, gain was reduced to 1000 for STN. Activa PC+S also has a data compression feature that we did not utilize, to avoid compression-associated reduction in the signal-to-noise ratio.

Data Analysis

Analyses were performed in Matlab using a combination of built in Matlab functions, EEGlab functions (Delorme and Makeig, 2004, Journal of neuroscience methods 134:9-21), and custom functions/scripts. Power spectral density calculations used the Welch method (pwelch in Matlab, with a window length of 512 ms and a FFT length of 256). The log of the PSD was then taken. To calculate coherence we first filtered both the ECoG and the LFP signals at frequencies ranging from 2-50 Hz, with a 2 Hz bandwidth using a two-way FIR1 filter (eegfilt in EEGlab). Complex signals were then obtained for each filtered signal by taking the Hilbert transform of the filtered signal. Coherence was calculated as the cross-spectrum of the two signals, normalized by each signal's auto-spectrum. For phase coherence, a similar procedure was used but instead of considering the entire complex signal, only the phase was extracted from each filtered signal using a Hilbert transform. Then the instantaneous phase difference between the two signals was taken (accounting for the fact that phase is a circular signal). Plots that show the instantaneous phase differences are derived from these phase difference values (i.e. instantaneous phase differences for the entire signal). To obtain phase coherence, the absolute value of the average of the instantaneous phase differences was calculated (i.e. the vector length, which signifies the consistency of the phase difference between regions).

Categorization of Files for Group Analysis

For each patient, we separated files into groups with and without dyskinesia based on the dyskinesia rating scales (Unified Dyskinesia Rating Scale (Goetz et al., 2008, Mov Disord 23:2398-2403)) obtained just before or just after the relevant data recording session, by a movement disorder neurologist, who did not analyze the electrophysiological data. If the Dyskinesia Rating Scale score was greater then zero for contralateral arm or trunk, the file was considered 'with dyskinesia', and if ratings were zero, the file was considered 'without dyskinesia'. To ensure correct categorization, we also evaluated videotapes performed during the data recording (performed during many, but not all, researcher-initiated data recordings,) to confirm presence or absence of dyskinesia. Recordings during rest, the iPad reaching task, and walking were included in the analysis. Additionally, for home recordings, if the patients noted that they were experiencing either 'dyskinesia' or 'involuntary movement' that was not tremor, the file was considered 'with dyskinesia', and if the patient's notes did not indicate dyskinesia, it was considered 'without dyskinesia'.

Recordings where the DBS settings were changed during the recording (wash-in or wash-out, or a change in DBS parameters) were excluded from the group analysis. Likewise, recordings from cortical contact pairs that never showed the narrowband gamma oscillation described in Results (regardless of dyskinesia status) were presumed to be insensitive detectors, and were excluded. (However, we conducted a control analysis including these recordings and results did not differ.) Additionally home recordings where the patient did not take notes or where notes were not clearly associated with a specific recording, were excluded. Finally 'montage recordings', where data were sampled at 422 Hz (instead of 800 Hz), were excluded.

Measurement of Gamma Oscillation Parameters

For each recording the maximum cortical or STN PSD peak between 62-83 Hz was extracted and a peak 'height' was calculating by subtracting the log PSD from the average log PSDs 5 Hz above and below the frequency of the peak. (In order to determine the frequency of the peak a normalization procedure was performed. First the spectrum was approximately flattened by fitting it to a $4^{th}$ order polynomial, excluding artifacts, to correct for the 1/f pattern (Pritchard, 1992, Int J Neurosci 66:119-129). Then the entire spectrum was normalized by subtracting the mean and dividing by the standard deviation across all frequencies. This method was used only to identify the frequency of the peak. The height of the peak at this frequency was calculated based on the original PSD as described above.) The method of quantifying gamma peak height is illustrated in FIG. 2B. The width of the peak at half the height was also calculated.

Coherence and phase coherence did not require a correction for the 1/f decrease because coherence values did not exhibit the strong 1/f decrease in amplitude present in the PSD (FIG. 2A). Additionally, because coherence is internally normalized, raw coherence values were used for the statistical analyses rather than first calculating the peak height relative to neighboring frequencies.

Measurement of Beta Oscillation Parameters

Due to the importance of beta band synchronization in the motor system and in PD in particular (Crone et al., 1998b; Hammond et al., 2007, Trends Neurosci 30:357-364), we also examined our four measures of interest (motor cortex PSD, STN PSD, coherence and phase coherence), in the beta frequency range (13-30 Hz). Log PSD values between 13-30 Hz were averaged to derive the PSD measures. Coherence values were derived in the same manner as described for the gamma oscillation analysis. Note that because of DBS artifacts in the beta range (at folded sub-harmonics), we included only recordings made in the absence of stimulation for this analysis.

Statistics

The values for all 4 variables of interest (motor cortex PSD, STN PSD, coherence, and phase coherence) were compared between groups (dyskinesia versus no dyskinesia) using a two-tailed, nonparametric Wilcoxon Rank Sum test. We tested this for each of the two patients separately (FIG. 3) as well grouped together (FIG. 2C). To determine if the stimulation artifact may be driving any results, we also ran the same analyzes including only recordings with DBS off (FIG. 4). To determine how well the height of the gamma PSD peak or the coherence values would work as classifiers for dyskinesia and to characterize the specificity and sensitivity of the biomarkers, we derived receiver operating characteristic (ROC) curves (Zwieg and Campbell, 1993). These were derived using the 'perfcurve' function in Matlab (FIG. 2D). Values were first fit to a logistical regression model ('fitglm') using a binomial distribution.

Figure 2:
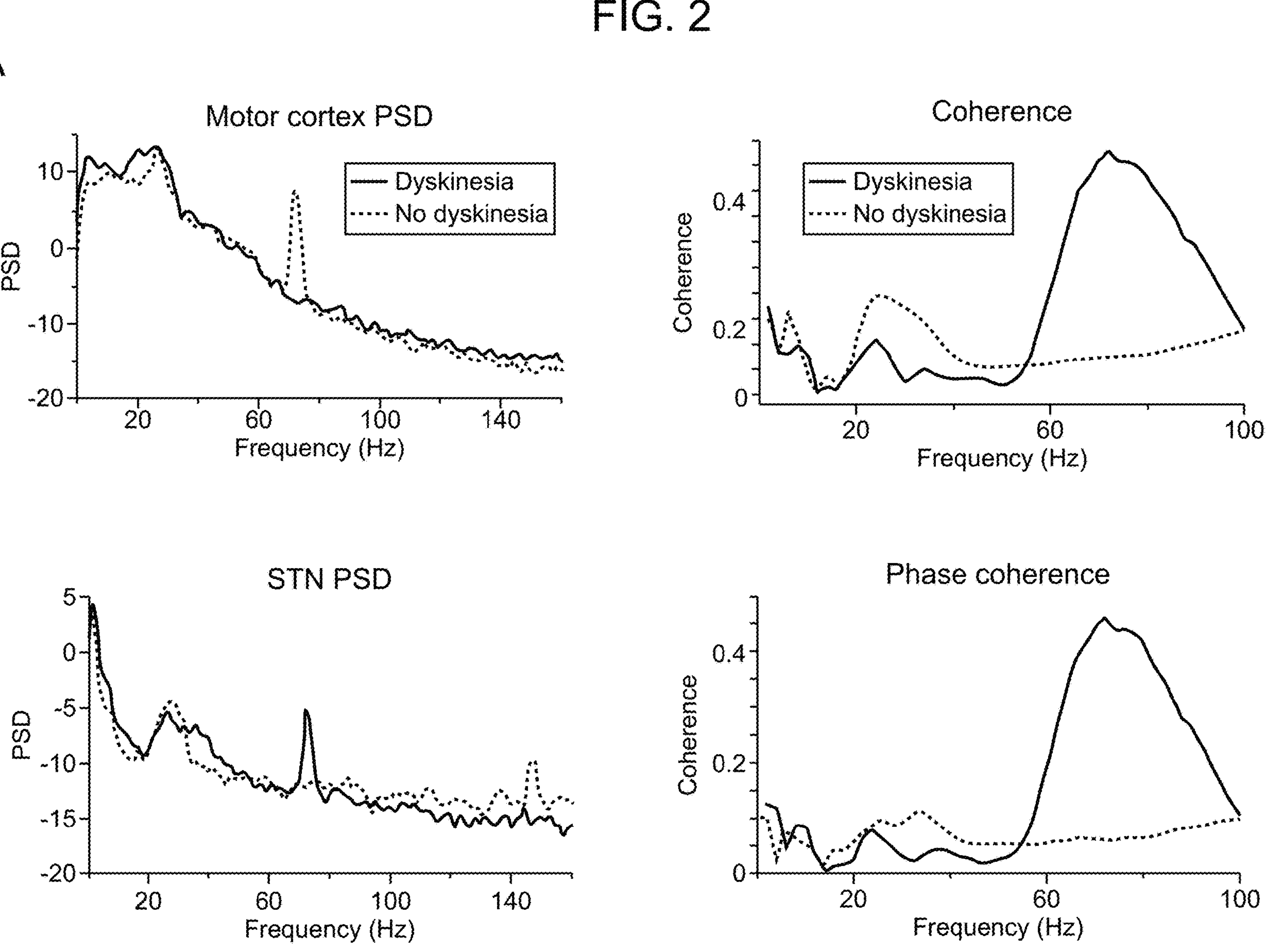
FIG. 2, Panels A-D show gamma oscillations distinguish the dyskinetic and nondyskinetic states.
Figure 2:
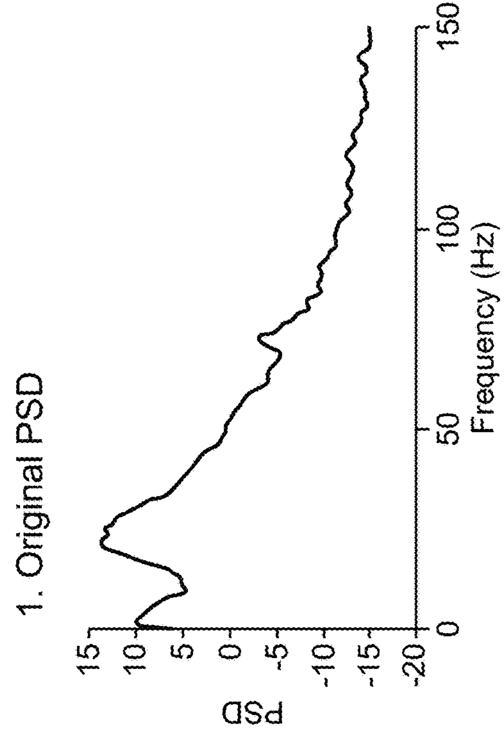
Figure 2:
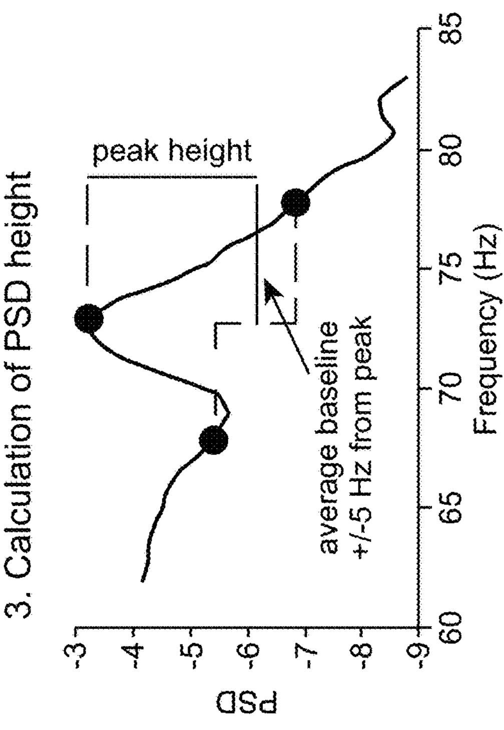
Figure 2:
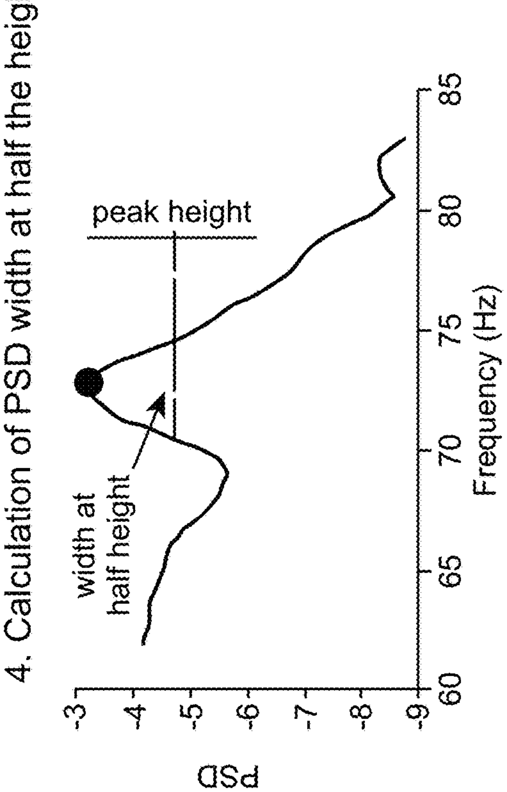
Figure 2:
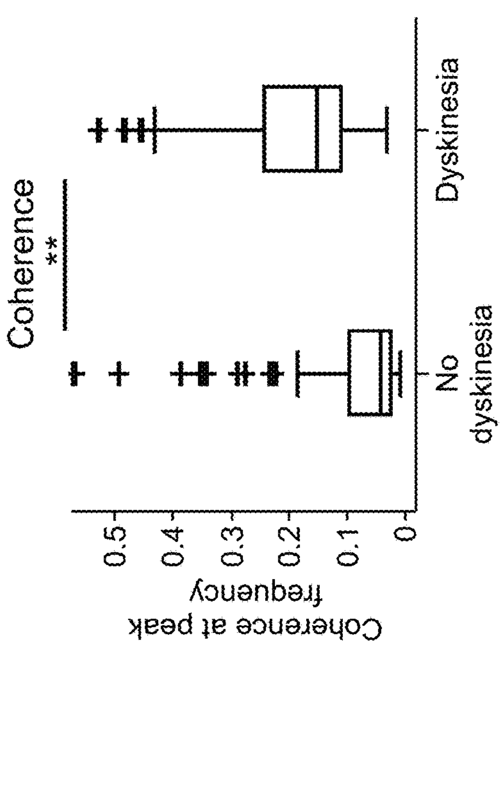
Figure 2:
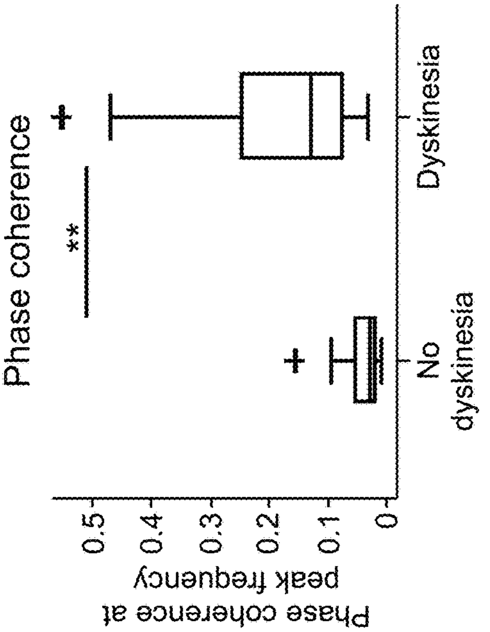
Figure 2:
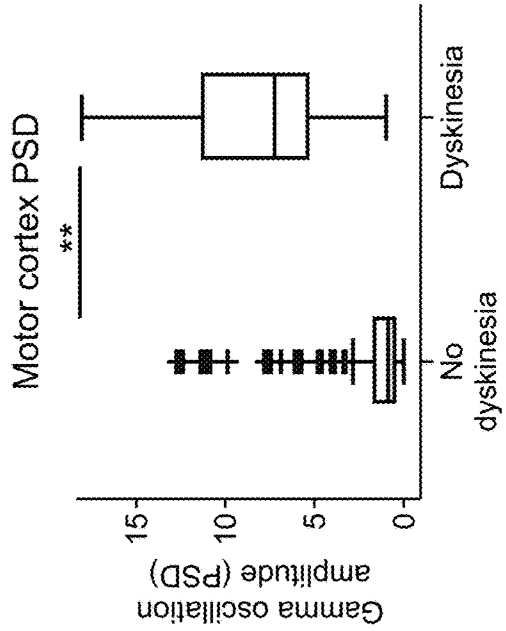
Figure 2:
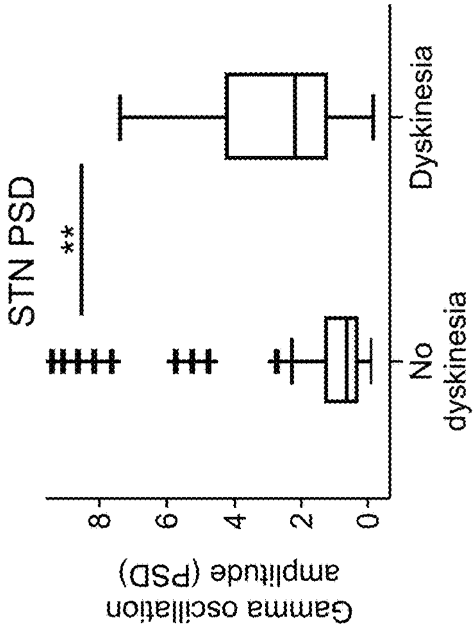
Figure 2:
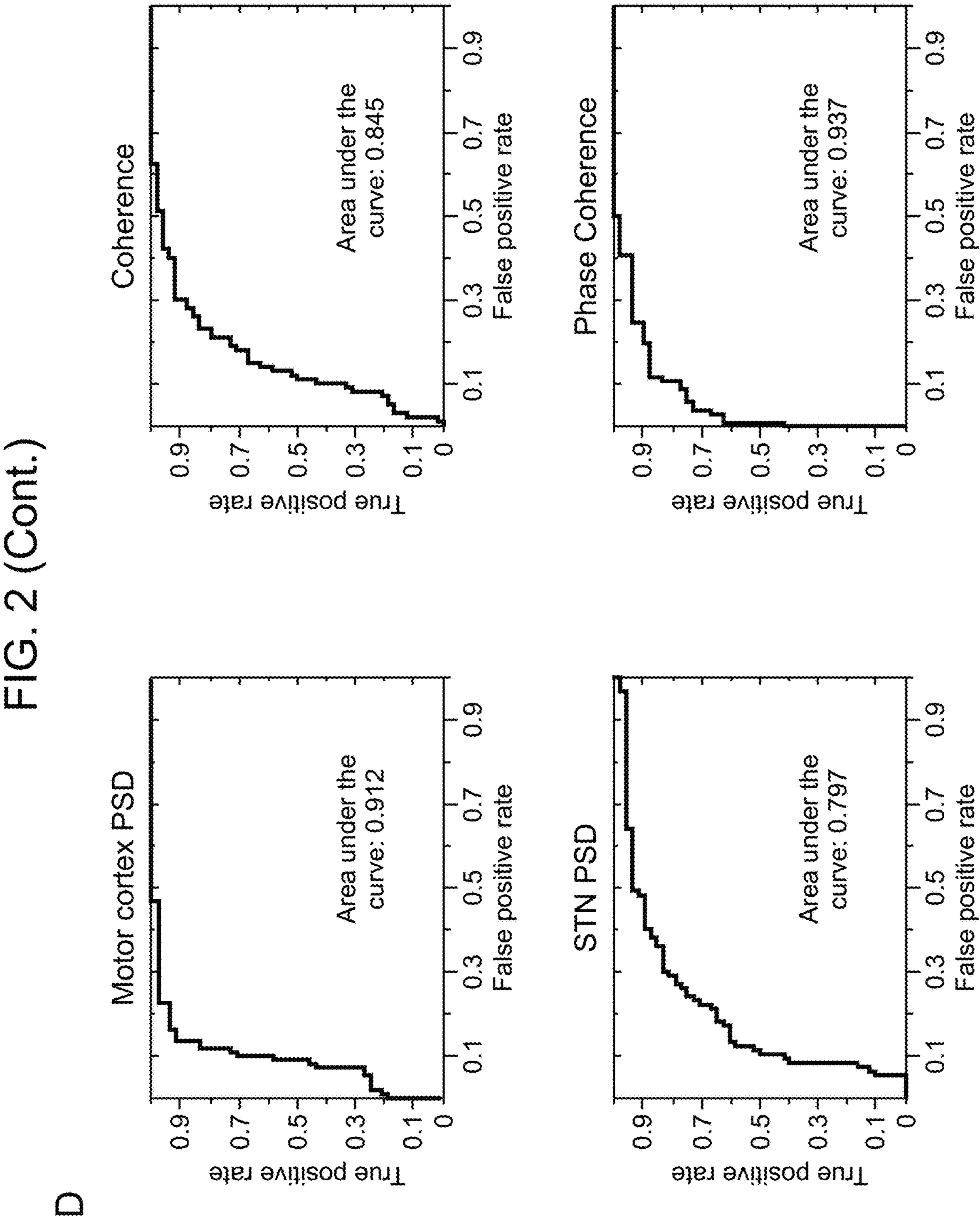

FIG. 2. Gamma oscillations distinguish the dyskinetic and nondyskinetic states. A. Example of motor cortex log PSD, STN log PSD, coherence, and phase coherence from patient 2 at rest (all on medications). PSD scale is $10*\log_{10}(\mu V^2/Hz)$. B. Schematic of PSD height and width calculation. Original PSDs (panel 1) were flattened and normalized (panel 2, see Methods) to identify the peak frequency in the 62-83 Hz range (red dot). The height of this peak was calculated by subtracting the original log PSD value at this frequency (red dot) from the average of the PSDs 5 Hz above and below the peak frequency (black dots, average indicated with green line). The height is indicated with the vertical black line (panel 3). The width of the peak at half the height was also calculated (red line in panel 4). For coherence, the maximum coherence in the 62-83 Hz range was used as the height. C. Group analysis for peak gamma amplitude. There was significantly higher gamma power during dyskinesia for each measure (Table 2). D. Receiver Operating Characteristic curves for each measure showing the false positive and true positive rates derived from fitting the data to a general linear model and examining rates for different classification threshold values for each biomarker.

TABLE 2

P-values and statistical parameters during dyskinetic versus nondyskinetic states (on and off DBS).

| Measure | Total number of recordings (pt 1/pt 2) | Number of recordings with dyskinesia total (pt 1/pt 2) | P-values total | P-values individual patients (pt1/pt2) | ROC AUC | True Positive/False Positive for optimal point |
|---|---|---|---|---|---|---|
| Motor cortex PSD | 159 (52/107) | 48 (23/25) | $2.22 \times 10^{-16}$ | $3.024 \times 10^{-7}$/ $2.48 \times 10^{-11}$ | 0.9123 | 0.9167/0.1351 |
| STN PSD | 148 (52/96) | 48 (23/25) | $5.122 \times 10^{-9}$ | $6.99 \times 10^{-4}$/ $1.5 \times 10^{-6}$ | 0.7973 | 0.5833/0.1200 |
| Coherence | 148 (52/96) | 48 (23/25) | $1.16 \times 10^{-11}$ | 0.08/ $4.72 \times 10^{-10}$ | 0.8452 | 0.667/0.1500 |
| Phase Coherence | 148 (52/96) | 48 (23/25) | $<1 \times 10^{-15}$ | $1.55 \times 10^{-8}$/ $8.30 \times 10^{-11}$ | 0.9371 | 0.7292/0.0400 |

ROC = receiver operator characteristic,
AUC = area under the curve.

between 62 and 83 Hz) distinguished the dyskinetic state from the non-dyskinetic state, with the strongest distinction for cortical PSD and cortex-STN phase coherence. Separation of biomarker amplitudes by dyskinesia status was also present when data from each patient were analyzed independently, with the sole exception of coherence in patient 1 (which was at the trend level, p=0.08, FIG. 3A, Table 2), showing the effects were not driven by a single patient. Separation of biomarker amplitudes also persisted when data were restricted to DBS-off (FIG. 4, Table 3), demonstrating that the effects were not driven by stimulation artifacts, which could have interfered with accurate peak height analysis in the gamma frequency range.

Figure 3:
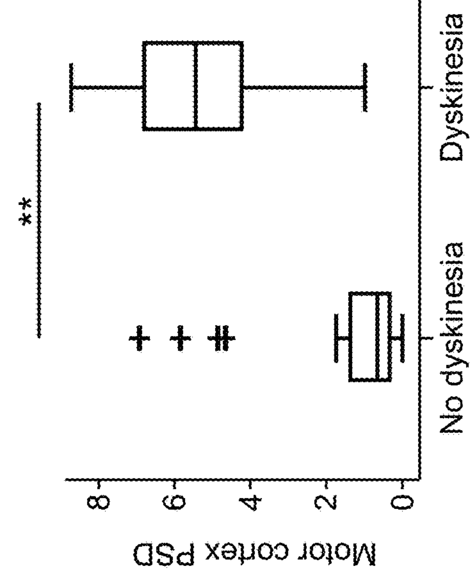
FIG. 3, Panels A-B provide grouped data from FIG. 2C segregated by patient (A, patient 1; B, patient 2).
Figure 3:
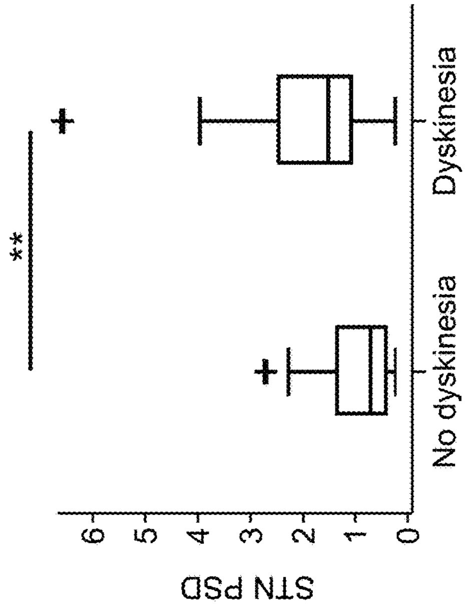
Figure 3:
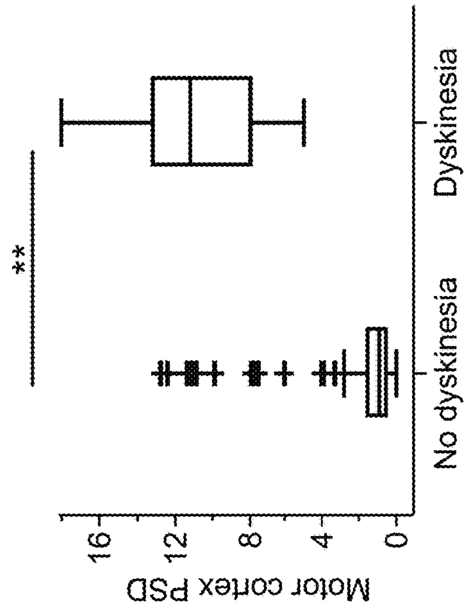
Figure 3:
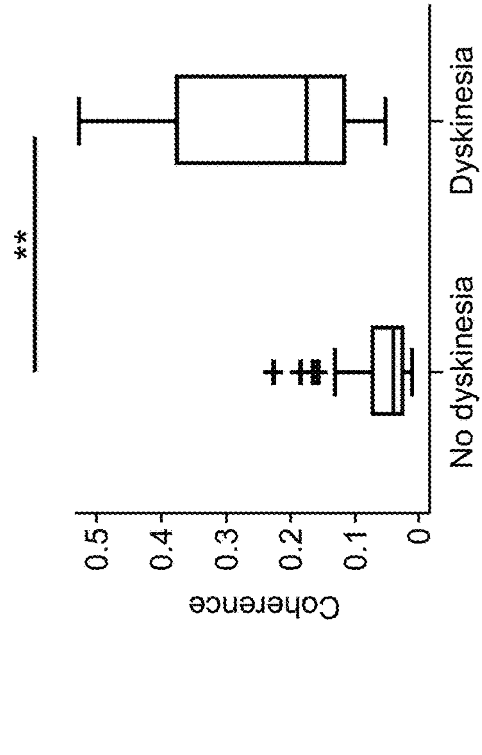
Figure 3:
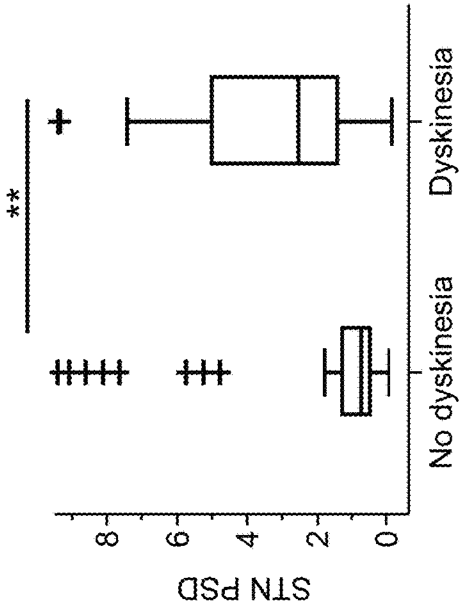
Figure 3:
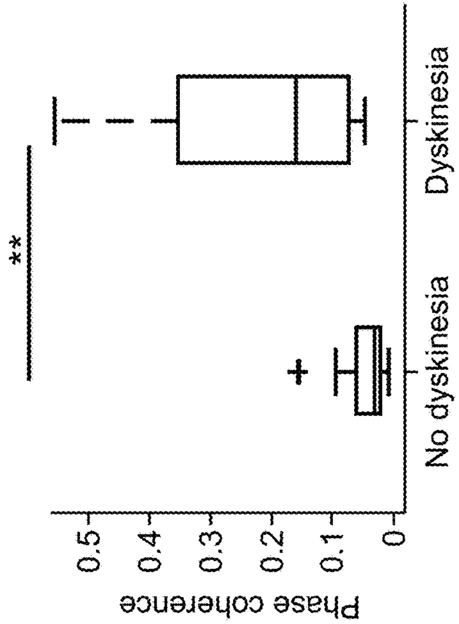
Figure 4:
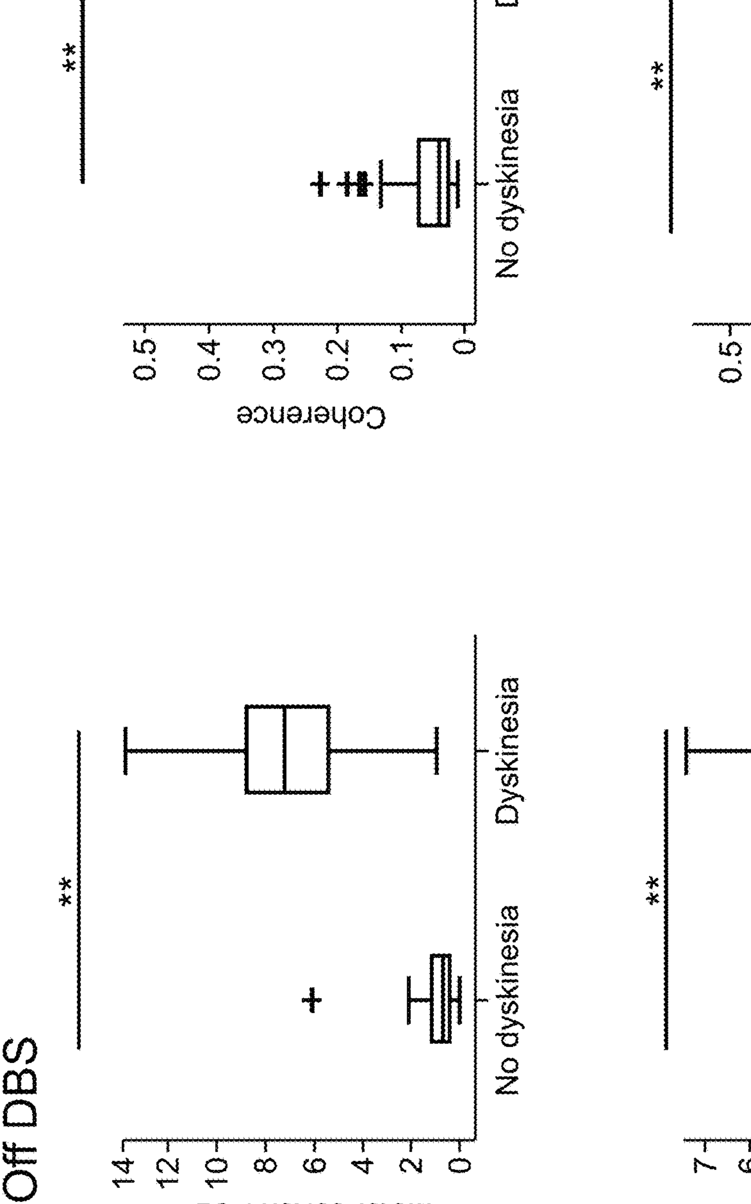
FIG. 4 provides grouped data from FIG. 2C for recording off DBS only.

FIG. 3. Grouped data from FIG. 2C segregated by patient (A, patient 1; B, patient 2), for each measure examined (motor cortex and STN PSD, coherence, and phase coherence). P-values are reported in Table 2.

FIG. 4. Grouped data from FIG. 2C for recording off DBS only. Values are significantly higher during dyskinesia for all measures, demonstrating that our findings are not driven by a stimulation artifact. P-values reported in Table 3.

TABLE 3

P-values and statistical parameters for gamma oscillation during dyskinetic versus nondyskinetic states (only data from off DBS).

| Measure | Total number of recordings | File number with dyskinesia | P-value total |
|---|---|---|---|
| Motor cortex PSD | 82 | 25 | $5.59 \times 10^{-12}$ |
| STN PSD | 80 | 25 | $2.97 \times 10^{-8}$ |
| Coherence | 80 | 25 | $2.86 \times 10^{-11}$ |
| Phase Coherence | 80 | 25 | $2.31 \times 10^{-11}$ |

Results

Recording Locations, Signal Characteristics, and Data Overview

Recording sites in cortex and basal ganglia, and example recordings from each site, are shown in FIGS. 1B and 1C. Average root mean square (RMS) voltage for recordings with DBS off, were 6.1 μV for STN and 19 μV for motor cortex. Signal amplitudes for recordings from both cortex and STN were stable for the 12 months of the study (FIG. 1D). The number of recordings used for group analyses are reported in Table 2. For each recording, the longest artifact-free segment of data was used for analysis. The mean duration of recordings (excluding artifacts) was 96.5 (SD=72) seconds (with a range of 28-302 seconds). There was no difference in the recording length for recordings with and without dyskinesia (p>0.88). One-hundred and seven of the recordings were initiated by study personnel during formal study visits at regular intervals, while fifty-two were initiated at home by the patients. Dyskinesia occurred almost exclusively in the on medication state, but could be present on or off of DBS.

Gamma Oscillations in Cortex and STN are Associated with Dyskinesia

Figure 5:
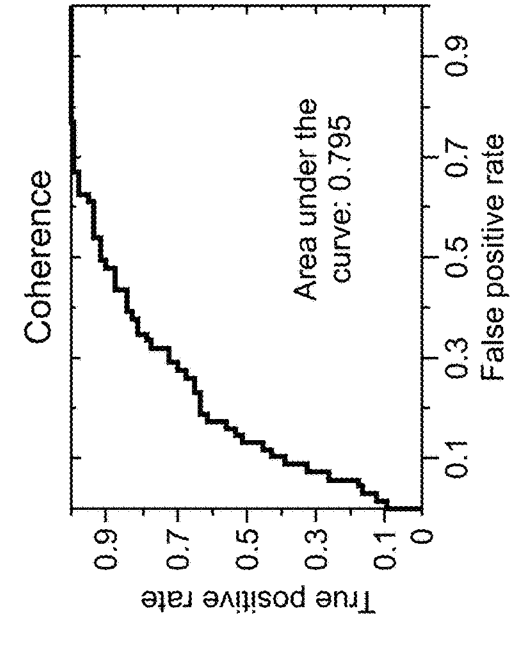
FIG. 5 depicts the gamma oscillation as a function of medication state.
Figure 5:
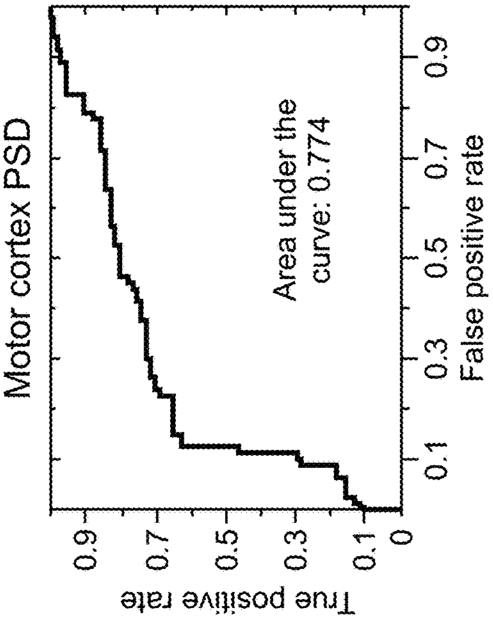
Figure 5:
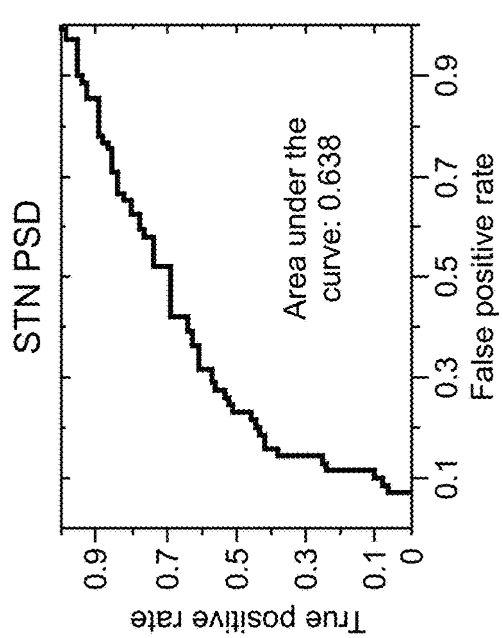

Visual inspection of power spectral density (PSD) plots for each cortical recording revealed that many of those collected during episodes of dyskinesia showed a discrete, narrowband peak (local maximum at peak frequencies between 62 and 83 Hz). A similar but smaller peak was often present in the STN, which had strong coherence with motor cortex (both magnitude and phase) in the same frequency range (example in FIG. 2A). To characterize the relationship of these oscillatory phenomena to the presence of dyskinesia, we quantified the oscillation (see FIG. 2B and Methods) and segregated its amplitude by dyskinesia status. Results are presented in FIG. 2C, with statistical details in Table 2. All four putative biomarkers (motor cortex and STN PSD, coherence, and phase coherence for the local maximum ROC curves are provided for each measure in FIG. 2D, and the area under the curve, and sensitivities and specificities for detection of the dyskinetic state are listed in Table 2. Consistent with the statistical evaluation above, the gamma oscillation amplitude in motor cortex, and gamma phase coherence between motor cortex and STN, were better classifiers for the presence or absence of dyskinesia than the gamma oscillation amplitude in STN or coherence between motor cortex and STN. Since dyskinesia occurred almost exclusively in the "on medication state", it is important to dissociate a medication effect from a dyskinesia effect. To show that the oscillatory biomarkers are more closely related to the dyskinetic state than the dopaminergic state (on versus off of dopaminergic medications), we also performed a ROC analysis for medication state (FIG. 5). This analysis included the same data shown in FIG. 2D, but grouped files according to medication status. For recordings in-clinic, "off medication" recordings were after withholding medications for at least 12 hours. Recordings that the patients initiated at home were considered 'on medication' unless patients indicated that they had been off medications overnight, since patients were maintaining their regular medication regimen. This analysis showed that the area under the curve for the ROC analysis derived by medication status is lower for all four gamma oscillation derived biomarkers, than when using the biomarkers to predict the presence or absence of dyskinesia.

FIG. 5. The gamma oscillation as a function of medication state. The oscillation is a relatively poor marker for medication state. Similar to FIG. 2D, except here, recordings are segregated based on medication state rather than presence or absence of dyskinesia. All home recordings were considered "on medication", unless patients indicated that they were off medications overnight, since patients were maintaining their regular medication regimen.

The fact that phase coherence distinguished the two clinical states to a greater degree than coherence suggests that the hyperkinetic state is more closely related to phase relationship between motor cortex and basal ganglia gamma oscillations, rather than to amplitude correlations between them. To visualize this effect, we pooled the instantaneous phase angles between motor cortex and STN for all time-points, all recordings, and both patients. We showed a consistent phase difference during dyskinesia, but not without dyskinesia (FIG. 6A). The mean phase angle during dyskinesia was 71 degrees. This phase relationship in the dyskinetic state persisted regardless of stimulation status (on, or off, FIG. 6B), demonstrating that the presence of stimulation artifact in those files recorded on-stimulation was not responsible for the observed consistency of the phase relationship between cortex and STN.

Figure 6:
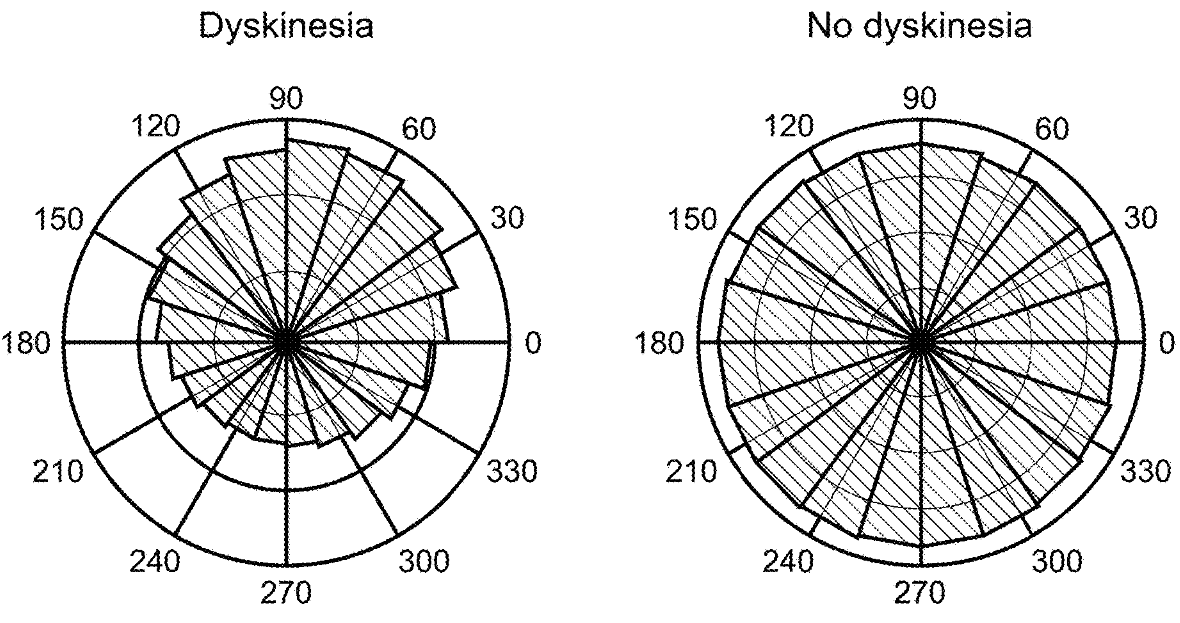
FIG. 6, Panels A-B depict STN-Motor cortex phase differences at the narrowband gamma frequency.
Figure 6:
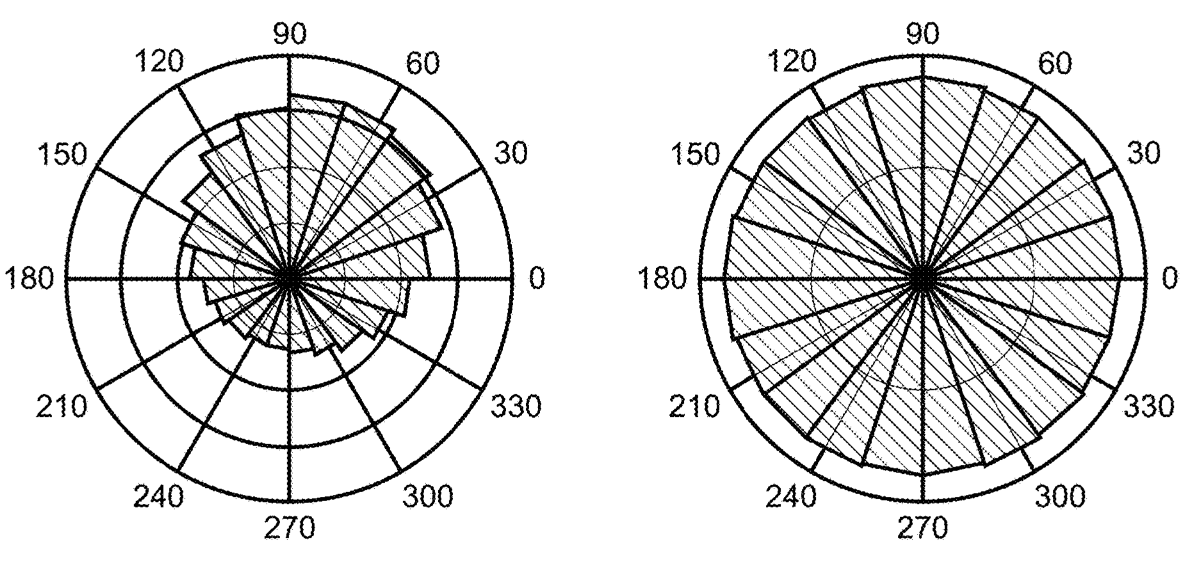

FIG. 6. STN-Motor cortex phase differences at the narrowband gamma frequency. A. Instantaneous phase differences between STN and motor cortex grouped for all recordings (on and off DBS) with and without dyskinesia. Number of sample points per bin are different for each plot due to differing amounts of data included for each. For the 'dyskinesia' recordings the outermost marker indicates 300,000 sample points and the second outermost indicates 200,000. For the 'no dyskinesia' recordings the outermost marker indicates 400,000 sample points and the second outermost indicates 300,000. B. Instantaneous phase differences between STN and motor cortex grouped for all recordings off DBS with and without dyskinesia. For the 'dyskinesia' recordings the outermost marker indicates 200,000 sample points and the second outermost indicates 150,000. For the 'no dyskinesia' recordings the outermost marker indicates 250,000 sample points and the second outermost indicates 125,000.

We also examined whether the height of the narrowband gamma oscillation correlated with dyskinesia severity. While we did observe a correlation ($r=0.63$, $p=3.58\times10^{-13}$, see FIG. 7), this effect was driven most strongly by presence versus absence of dyskinesia, rather than by its severity. This is consistent with the observation in rodents that the relationship between gamma power and dyskinesia severity is sigmoidal (Halje et al., 2012, J Neurosci 32:16541-16551).

Figure 7:
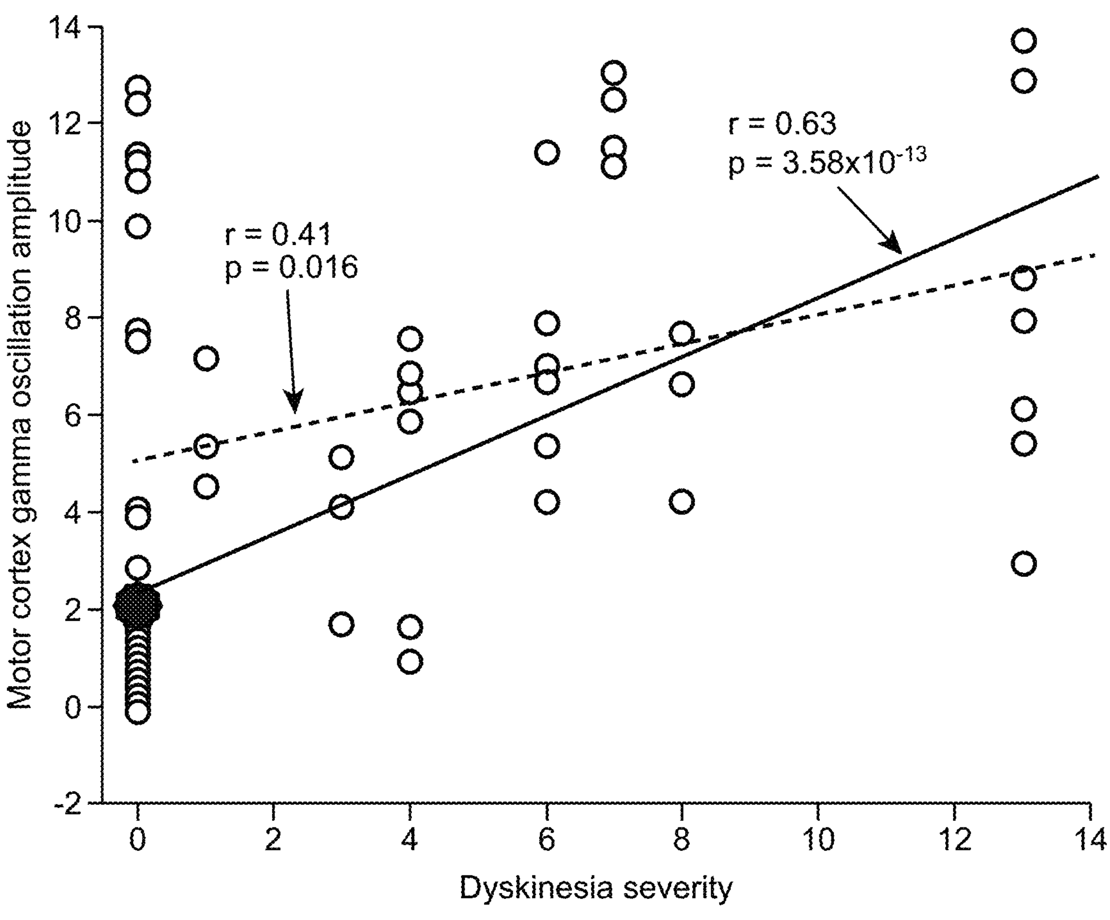
FIG. 7 shows correlation between dyskinesia severity and gamma oscillation amplitude.

FIG. 7. Correlation between dyskinesia severity and gamma oscillation amplitude. There is a correlation between dyskinesia severity (measured with dyskinesia rating scale, see Methods), and peak height of gamma oscillation in motor cortex ($r=0.63$, $p=3.58\times10^{-13}$, Spearman correlation, indicated with red regression line). However, this effect was mostly driven by presence or absence of dyskinesia (when files with no dyskinesia were excluded $r=0.41$, $p=0.016$, Spearman correlation, indicated with black regression line). This observations is consistent with a bimodal or sigmoidal relationship between dyskinesia severity and gamma oscillation height (Halje et al., 2012, supra). Only in-clinic recordings were included in this analysis (where the dyskinesia rating scale was available, 107 recordings total). The sum of dyskinesia severity from all effectors measured with the dyskinesia rating scale (arms, legs, trunk, neck and face) was derived to quantify dyskinesia severity. Average value for recordings without dyskinesia is indicated with the large yellow circle.

Beta Oscillations in Cortex and STN and Association with Dyskinesia

Figure 8:
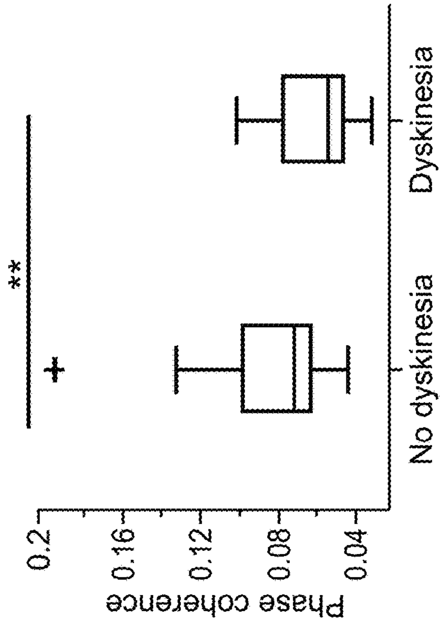
FIG. 8 shows beta oscillations in the dyskinetic and nondyskinetic states.
Figure 8:
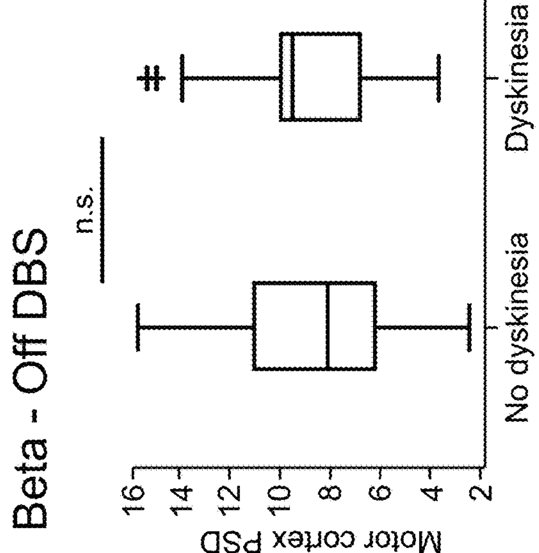
Figure 8:
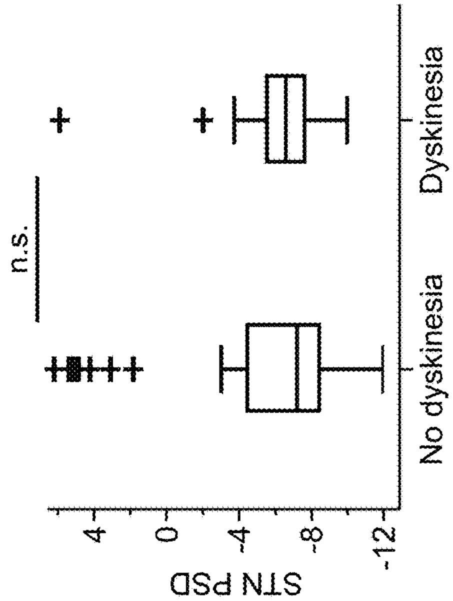

In contrast to the gamma oscillation, in the beta range neither motor cortex PSD, STN PSD, nor coherence distinguished the dyskinetic from the nondyskinetic states (FIG. 8). There was a significant difference in phase coherence ($p=7.24\times10^{-4}$), with lower beta phase coherence between STN and motor cortex when dyskinesia was present compared to when it was absent (the opposite pattern that we observed for the gamma oscillation.) Of note we also repeated the beta range analysis with recordings categorized by medication (as performed in FIG. 5). For this analysis we also found a significant difference in phase coherence ($p=0.012$) with lower phase coherence between motor cortex and STN when patients were on medications compared to off. We also observed lower STN PSD when patients were on medications compared to off ($p=0.0356$), as has been observed in previous studies (Priori et al., 2004; Kühn et al., 2006).

FIG. 8. Beta oscillations in the dyskinetic and nondyskinetic states. Grouped analysis analogous to that shown in FIG. 2C, except focusing on the beta range (13-30 Hz). This analysis includes only recordings with DBS off, to avoid artifacts caused by DBS sub-harmonics in the beta range. There are no significant differences except for decreased phase coherence between motor cortex and STN during dyskinesia ($p=7.24\times10^{-4}$). n.s.=not significant.

Relation Between Gamma Oscillation Characteristics in Cortex Versus STN During Dyskinesia The relationship between gamma oscillatory characteristics in cortex versus STN, for DBS off recordings, is described in Table 4.

TABLE 4

Gamma oscillation characteristics for motor cortex ECoG and STN LFP power spectra off stimulation.

| Measure | Peak Frequency | Peak Height | Peak Width |
|---|---|---|---|
| Motor cortex | 74.56 (SD = 3.59) Hz | 7.25 (SD = 3.01) $10\times\log_{10}(\mu V^2/Hz)$ | 5.15 Hz (SD = 1.28 Hz) |
| STN | 72.95 (SD = 3.30) Hz | 3.01 (SD = 2.14) $10\times\log_{10}(\mu V/^2Hz)$ | 4.37 Hz (SD = 1.47) |

Peaks were of greater amplitude in cortex compared to STN. The peak frequency varied between recordings, but their distributions in the two patients studied overlapped (FIG. 9A). Of note, the exact frequency of the gamma peak may be related to the time of recording relative to levodopa dose (Halje et al., 2012, supra). There was a significant correlation (Pearson's $r=0.597$, $p=0.0016$) between the frequency of the gamma peak in cortex and STN (FIG. 9B). Although only two subjects in the study (1 and 2) had a sufficient number of recordings in the dyskinetic state for statistical analyses (explained further in methods), very similar frequency and amplitude characteristics of the dyskinesia-associated cortical PSD peak were seen in two other subjects who had a small number of high signal-to-noise ratio recordings in the dyskinetic state (examples in FIG. 10). The fifth study subject had no dyskinesia after DBS implantation, and did not have a narrowband gamma oscillation in cortex or STN.

Figure 9:
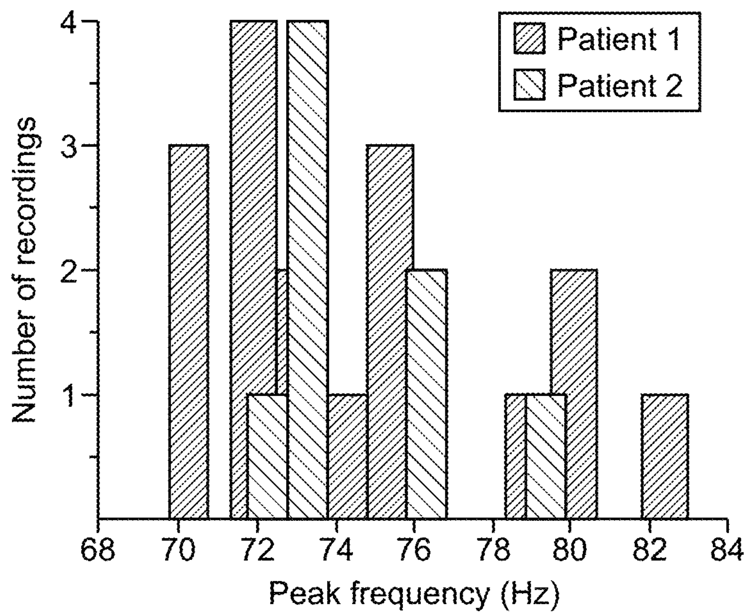
FIG. 9, Panels A-B depict characterization of peak frequency of the gamma oscillation.
Figure 9:
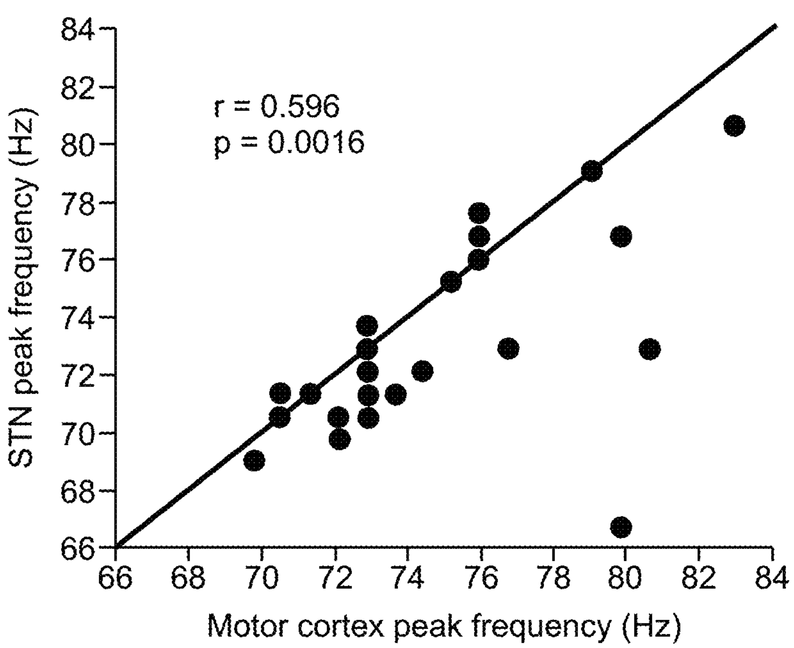

FIG. 9. Characterization of peak frequency of the gamma oscillation. A. Frequencies at which the gamma oscillation occurred off DBS for patients 1 and 2. There does not appear to be a "characteristic frequency" within the gamma range for each patient. B. Correlation between frequency of gamma oscillation in motor cortex versus STN for stimulation off files (Pearson's r=0.597, p=0.0016). Y=x line is shown in red.

FIG. 10. Example recordings from patients not included in the grouped statistical analysis. Examples from patients 3 (A) and 4 (B) during episodes of dyskinesia versus no dyskinesia (or minimal dyskinesia). Both recordings are on DBS. Note that in panel A the data were recorded at 422 Hz during a montage recording. Panel B data were recorded at 800 Hz as usual. PSD scale is $10*\log_{10}(\mu V^2/Hz)$.

The Gamma Oscillation and Voluntary Movement

In order to be of optimal utility as a driver of closed loop deep brain stimulation, a biomarker of abnormal movement should not be strongly affected by normal movement. To assess the effect of voluntary movement on gamma oscillation derived biomarkers, we conducted an analysis similar to FIG. 2B but separated recordings that included voluntary movement (walking or performing an arm movement (iPad) task) from those without voluntary movement (FIG. 11). In the dyskinetic state there were no significant differences in the gamma oscillation amplitude for any measure between recordings obtained with and without voluntary movement. In contrast, the difference in the gamma oscillation for all comparisons with and without dyskinesia was highly significant.

FIG. 11. Amplitudes of dyskinesia biomarkers related to the gamma oscillation are minimally affected by voluntary movement. Biomarker amplitudes associated with each recording were segregated both by presence or absence of dyskinesia, and presence or absence of voluntary movement (i.e. 'walking' or 'IPad' recordings compared to other recordings). There were 20 or more recordings included in the analysis for each condition. Dataset is the same as in FIG. 2C. Except for coherence in the non-dyskinetic state (p=0.0063), movement condition had no effect on biomarker amplitude. n. s.=not significant.

Figure 12:
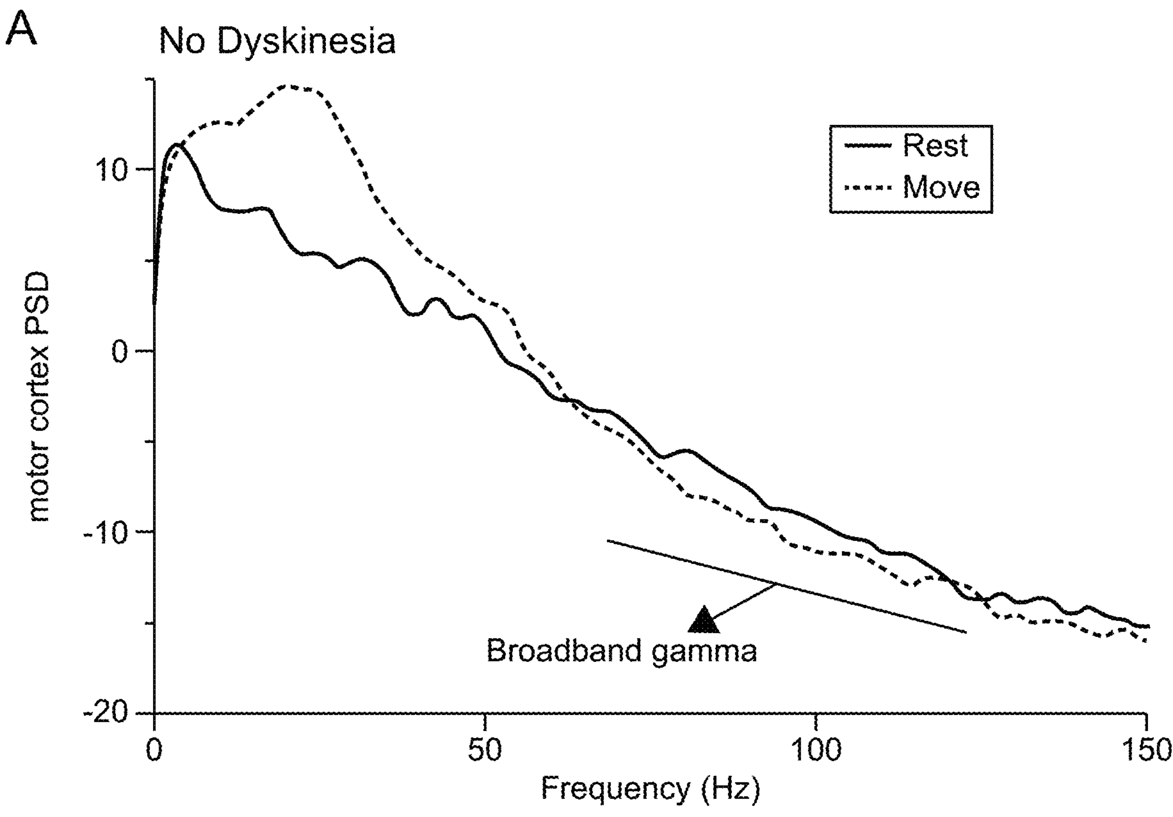
FIG. 12, Panels A-B depict broadband gamma versus gamma oscillation.
Figure 12:
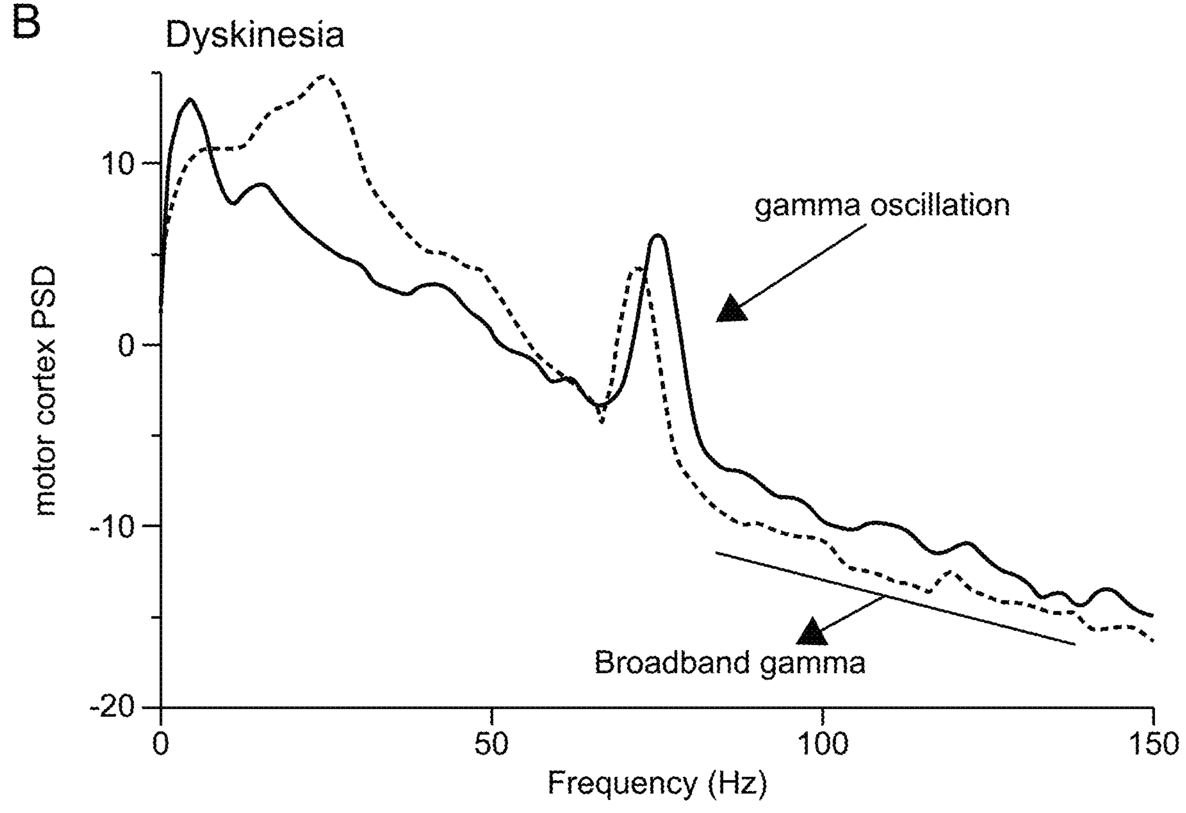

In sensorimotor cortex, a broadband power increase is known to be associated with movement (Crone et al., 1998a; Miller et al., 2007, Journal of Neuroscience 27:2424-2432), however this gamma increase is over a much broader frequency range (usually 50-250 Hz) and likely has a different etiology than the narrowband peak we see here (Manning et al., 2009, J Neurosci 29:13613-13620). Additionally the movement-related broadband power change is small in amplitude compared to the height of the peak associated with dyskinesia (FIG. 12). This point is developed further in the Discussion.

FIG. 12. Broadband gamma versus gamma oscillation. Example of broadband gamma increase during movement when patient 2 was not dyskinetic (A) and when he was dyskinetic (B). Note that in panel B the gamma oscillation is also apparent, and distinguishable from the broadband increase. Plots are derived from 20 trials of the iPad reaching task (analysis contains 2 seconds of movement, 2 seconds of rest, for each trial). In panel A the patient was off medications, in panel B they were on medications, in both examples they were off DBS. PSD scale is $10*\log_{10}(\mu V^2/Hz)$.

Localization of Cortical Gamma Oscillation

Precise localization of cortical contact(s) over the region of the strongest gamma oscillatory signal will be important for clinical use of a cortical detector in feedback controlled DBS. In patient 2 we recorded files from all possible cortical contact pairs ('montage recordings', see Methods), during dyskinesia and observed that the dyskinesia-associated narrow-band gamma power increase was spatially specific to one contact common to all bipolar pairs showing a strong gamma oscillation (contact 11, AC-PC coordinates: −38.02, −6.59, 64.21). This contact localized to the anterior part of precentral gyms, extending over the precentral sulcus (FIG. 13).

Figure 13:
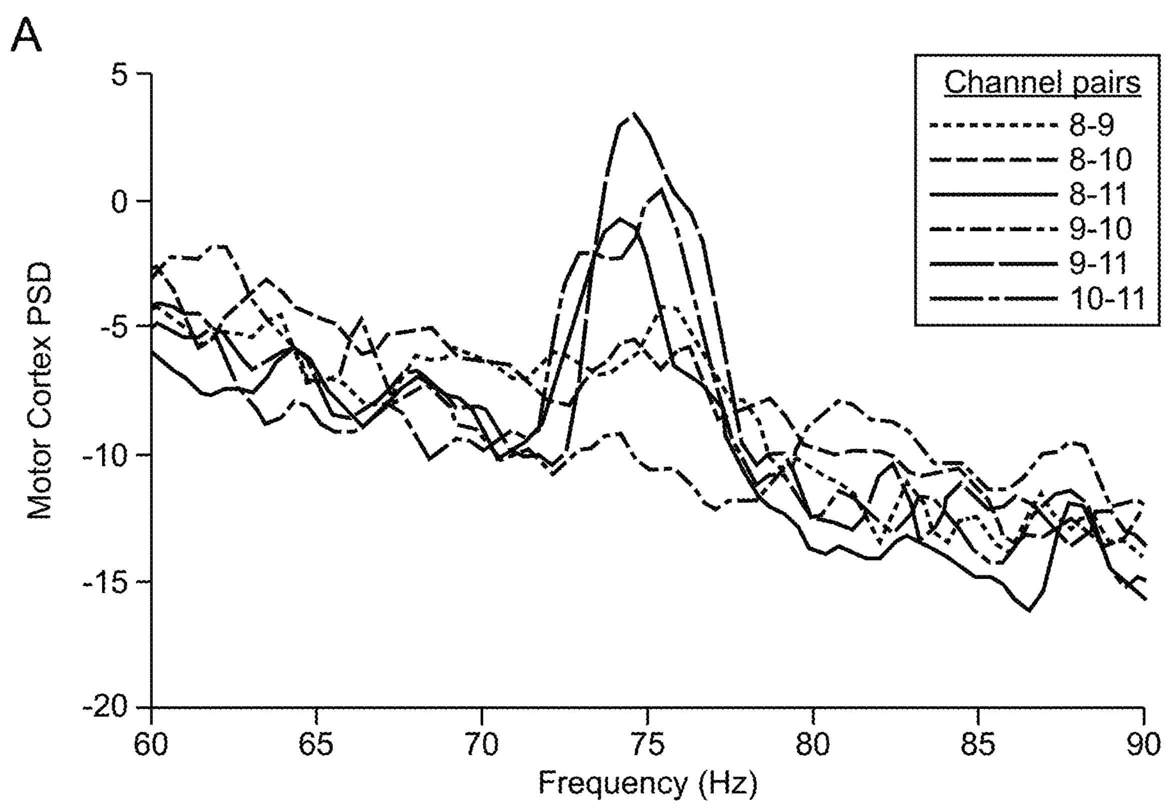
FIG. 13, Panels A-B depict optimal recording location for cortical gamma oscillations.
Figure 13:
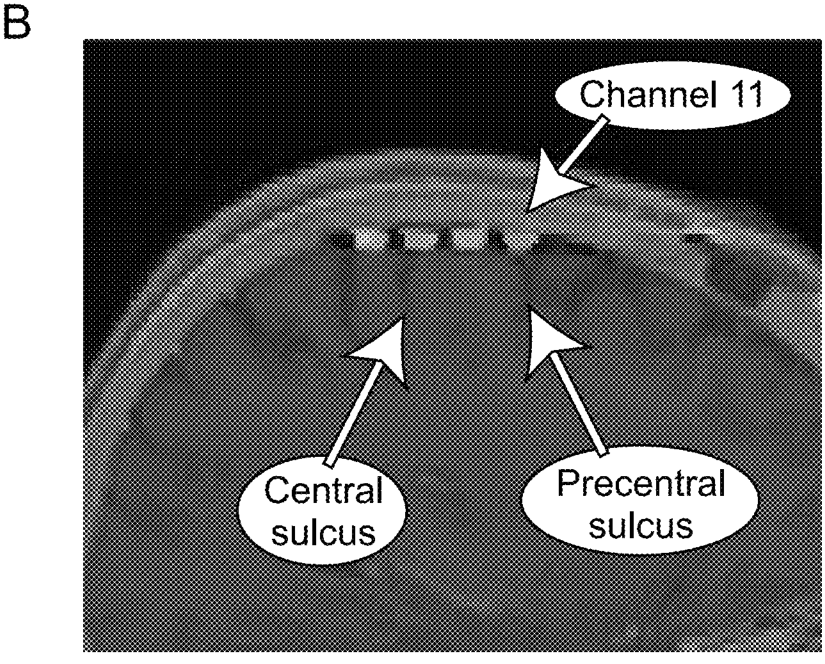

FIG. 13. Optimal recording location for cortical gamma oscillations. A, set of recordings from all contact pairs recorded sequentially (over a time period of 3 minutes) from patient 2 during dyskinesia. This recording was obtained with a sampling rate of 422 Hz (required to obtain a rapid sequential "montage recording" across all possible contact pairs), with DBS off.

The peak is most strongly observed in contact pairs that include contact 11. PSD scale is 10*log 10(μV2/Hz). B. Fusion of intraoperative CT with preoperative MRI, showing contact locations with respect to gyral anatomy. Contact 11 (white arrow) is located over the anterior portion of the precentral gyms, as well as precentral sulcus.

STN Stimulation Entrains Cortical Gamma at Half the Stimulation Frequency

STN stimulation is known to be able to suppress or exacerbate dyskinesia in PD, depending on exact stimulation parameters and contact locations (Zheng et al., 2010, Stereotact Funct Neurosurg 88:29-34; Oyama et al., 2012, Parkinsonism Relat Disord 18:814-818). Both Patients 1 and 2 often experienced dyskinesia both on and off stimulation. When dyskinesia occurred in the on-stimulation state, the cortical gamma peak always occurred at half the stimulation frequency (example in FIG. 14A). This is unlikely to be due to stimulation artifact because it was not present when stimulation was delivered at the same settings, but in the absence of dyskinesia (example in FIG. 14B). Moreover, the distribution of phase angles between STN and motor cortex in the dyskinetic state, at half stimulation frequency, were similar for stimulation-on recordings compared to stimulation-off recordings. In contrast, a more narrow (presumed artifactual) phase angle distribution is observed at the actual frequency of stimulation and at folded sub-harmonics of stimulation frequency (FIG. 14D). These findings are consistent with reports of "partial entrainment" of neuronal discharge by STN DBS at therapeutic frequencies (Garcia et al., 2003, J Neurosci 23:8743-8751; Hashimoto et al., 2003, J Neurosci 23:1916-1923; Li et al., 2012, Neuron 76:1030-1041; Agnesi et al., 2015). Our findings suggest that when this entrainment occurs in the frequency range associated with dyskinesia, DBS cannot suppress the dyskinetic state. As a proof of principle we showed that the frequency at which the peak occurred could be moved by changing the stimulation frequency, in this example from 65 Hz with 130 Hz stimulation to 75 Hz with 150 Hz stimulation, (FIG. 14C), and peak shifts during stimulation wash in and wash out (FIG. 14E-F). These changes in the peak frequency of the gamma oscillation did not produce observable changes in the clinical phenomenology of the dyskinetic movements.

Figure 14:
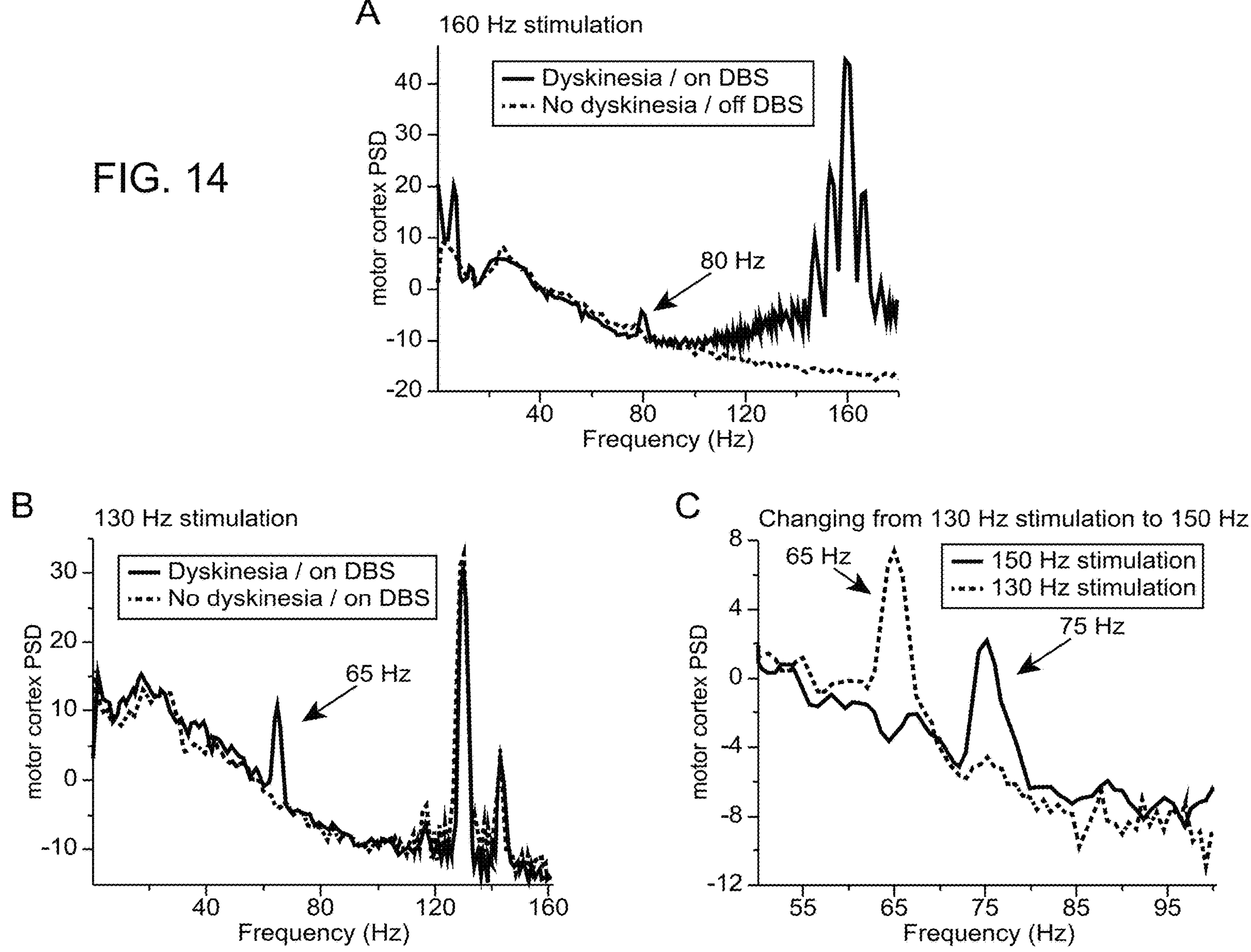
FIG. 14, Panels A-F illustrate that DBS entrains the gamma oscillation at half the stimulation frequency.
Figure 14:
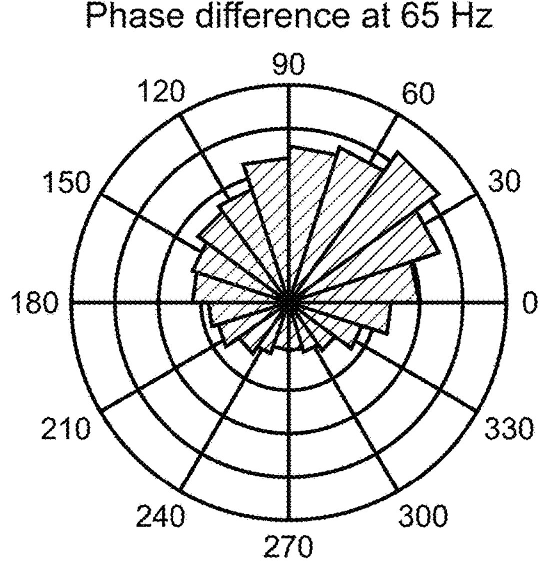
Figure 14:
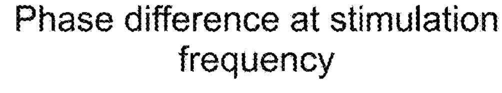
Figure 14:
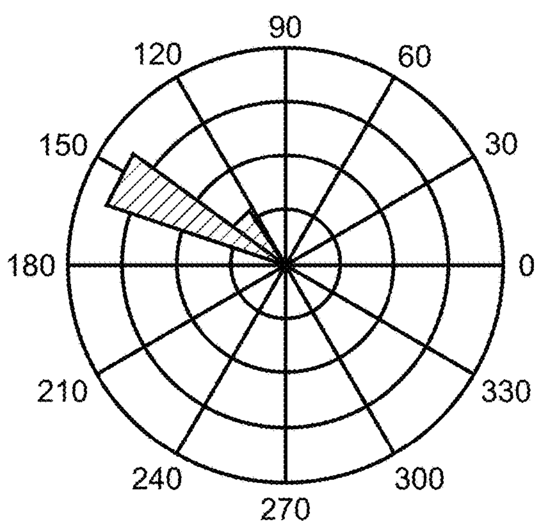
Figure 14:
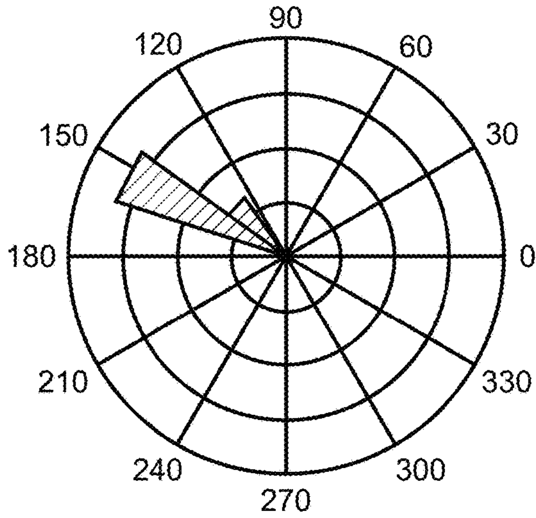
Figure 14:
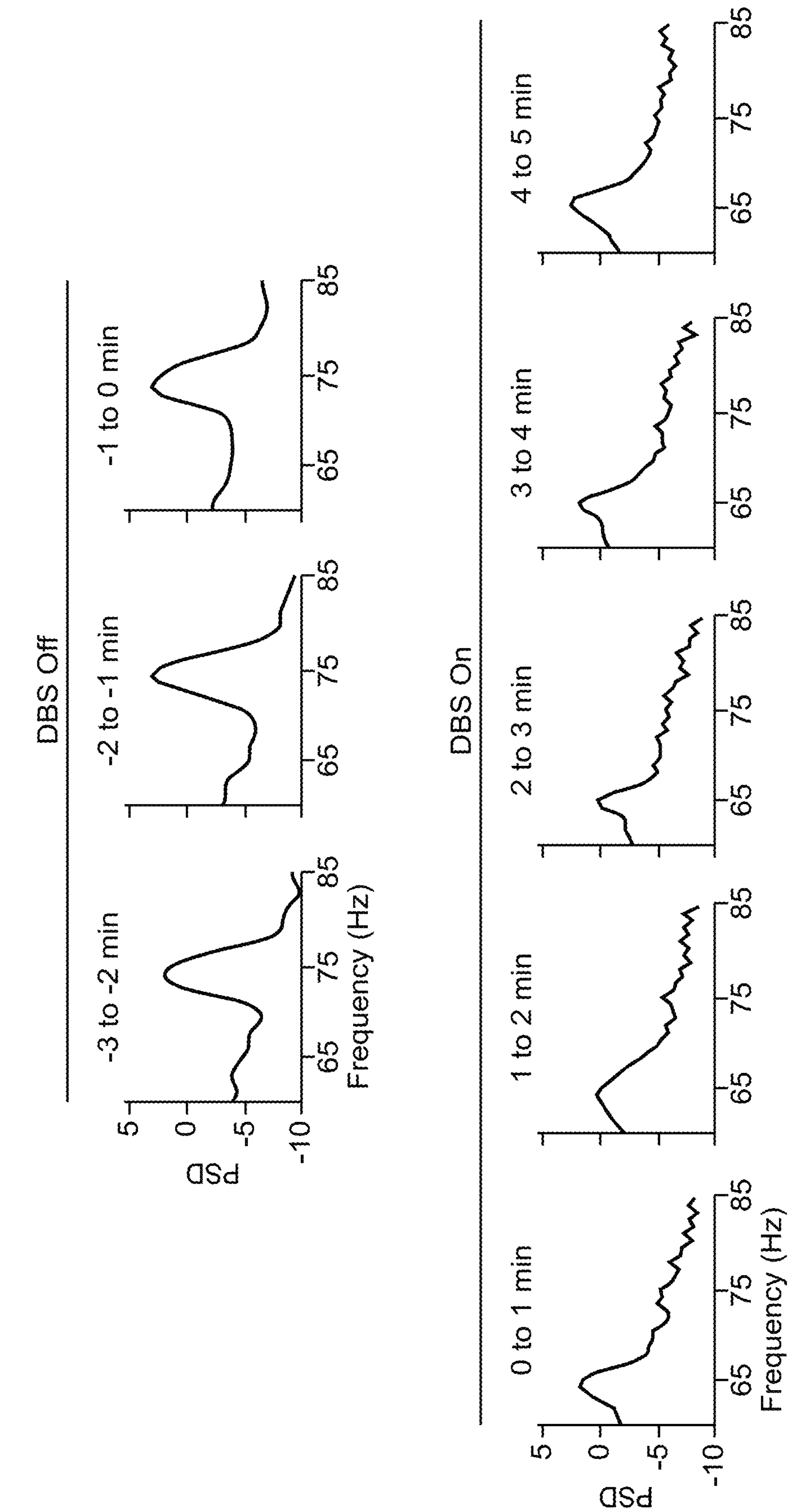
Figure 14:
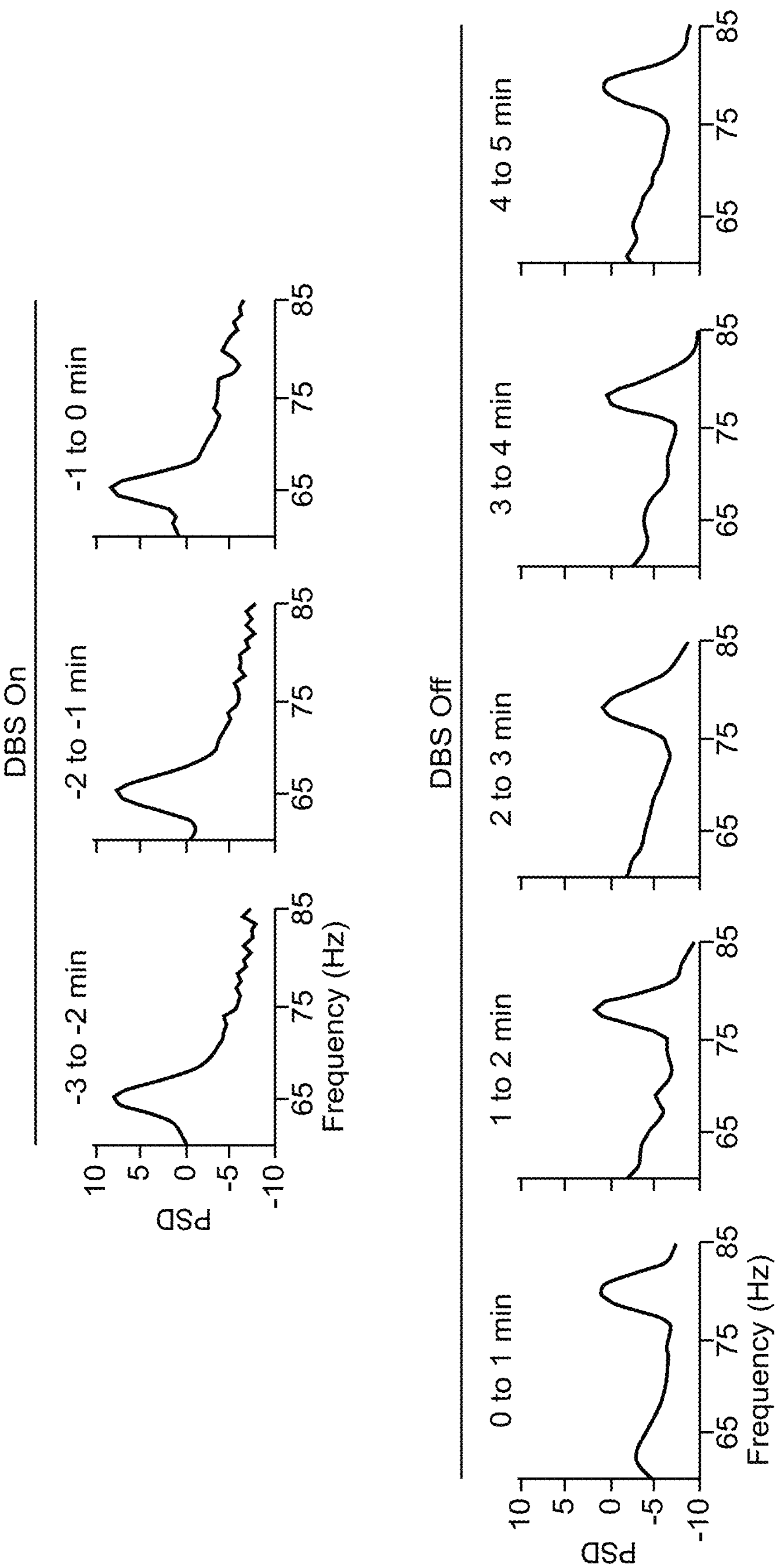

FIG. 14. DBS entrains the gamma oscillation at half the stimulation frequency. A. Example from patient 1 during dyskinesia that was present on DBS (160 Hz), and absent off DBS. PSD scale is $10*\log_{10}(\mu V^2/Hz)$. B. Example from patient 2 with and without dyskinesia on DBS (130 Hz). Note that the gamma oscillation is not present in the recording without dyskinesia, despite a similar stimulation artifact, arguing against the artifact driving the effect. C. When DBS frequency is changed (from 130 Hz to 150 Hz), the gamma oscillation also changes (from 65 Hz to 75 Hz). Example from patient 2. D. Instantaneous phase difference between STN and motor cortex for a file recorded during DBS while the patient was experiencing dyskinesia. The gamma oscillation has a similar distribution and phase angle as the off stimulation recordings (compare FIG. 6B). In contrast, the same measures at the stimulation frequency (130 Hz) or a folded sub-harmonic (116 Hz) have a more narrow distribution, consistent with an artifactual source. Example from patient 2. E. The frequency of the gamma oscillation during DBS wash-in moves from ~75 Hz, to half the stimulation frequency (65 Hz, at 130 Hz stimulation). F. During wash-out the gamma oscillation moves back to ~75-80 Hz. Both E and F are from patient 2.

We studied circuit mechanisms of dyskinesia using a novel, totally implanted chronic multisite brain-recording device in humans with PD. Motor cortex ECoG and STN LFPs were analyzed in two patients over one year, revealing a narrowband network oscillation between 60 and 90 Hz. This oscillation is closely associated with dyskinesia. When dyskinesia is present during DBS, this oscillation is entrained at a subharmonic of the stimulation frequency. These findings provide a mechanistic basis for a debilitating adverse effect of therapy in PD and suggest algorithms for feedback-controlled neuro-stimulation.

Narrowband Gamma Rhythms Versus Broadband Gamma Activity

The narrowband 60-90 Hz rhythm studied here should be distinguished from cortical "broadband gamma", which is a wideband phenomenon (typically 50-200 Hz) that tracks local activation and likely reflects underlying spiking activity rather than a narrowband oscillatory rhythm (Ray et al., 2008, J Neurosci 28:11526-11536; Manning et al., 2009; Scheffer-Teixeira et al., 2013, J Neurosci 33:1535-1539). Broadband gamma activity may play a role in the pathophysiology of the off medication parkinsonian state, where akinesia is prominent and dyskinesia is absent. In this state, there is elevated resting broadband gamma in motor cortex (Crowell et al., 2012, supra; Rowland et al., 2015, Frontiers in human neuroscience 9:512), as well as excessive coupling of broadband gamma to the phase of the beta rhythm (de Hemptinne et al., 2013, supra). Broadband gamma is also modulated by voluntary movement (Crone et al., 1998a; Miller et al., 2007). In contrast, the narrowband gamma oscillation elucidated in the present work is likely a manifestation of neuronal oscillations, is relatively unchanged by voluntary movements, and is associated with a hyperkinetic, rather than a bradykinetic, state. For illustration of this distinction see FIG. 12. We utilize the terms "oscillation" or "rhythm" to make the distinction between narrowband phenomena versus arrhythmic broadband phenomena.

Functional Role of Gamma Oscillations and Relationship to Hyperkinetic Movements Previous work has shown narrowband gamma oscillations to be a normal feature of cortical function, implicated in numerous cognitive processes, which may act to "bind" cortical regions together based on their phase relationships (Fries, 2009; Sohal, 2012, Biol Psychiatry 71:1039-1045). Alterations in cortical gamma rhythms have been implicated in diseases including autism and schizophrenia (Sohal, 2012). Altering the balance of excitatory and inhibitory activity in the cortex regulates these rhythms (Yizhar et al., 2011, Nature 477:171-178). Interactions of inhibitory fast spiking interneurons play a critical role (Sohal, 2012; Salkoff et al., 2015, J Neurosci 35:10236-10251), and these generators may be regulated by neuromodulators including acetylcholine (Teles-Grilo Ruivo and Mellor, 2013, Front Synaptic Neurosci 5:2) and serotonin (Puig et al., 2010, J Neurosci 30:2211-2222).

In subcortical regions, invasive human LFP recordings from temporarily externalized DBS leads have detected gamma rhythms in STN (Cassidy et al., 2002; Alonso-Frech et al., 2006; Trottenberg et al., 2006, Experimental neurology 200:56-65), globus pallidus (Weinberger et al., 2012), and thalamus in both PD patients and in patients with several non-parkinsonian conditions (Kempf et al., 2009). In PD patients, the subcortical gamma oscillation is present mainly in the on-medication state. However, the relationship to dyskinesia has been unclear. A combined STN LFP/magnetoencephalography study in PD detected a cortical gamma rhythm and STN-cortical coherence, at the onset of voluntary movement, supporting a prokinetic role for the gamma oscillation (Litvak et al., 2012). Here we are able to characterize a gamma oscillation that propagates through motor cortex and basal ganglia and is strongly associated with dyskinesia. Given the presence of gamma oscillations in the thalamus in several non-dyskinetic conditions (Kempf et al., 2009), it is possible that dyskinesia arises when subcortical gamma rhythms are excessively propagated throughout the basal ganglia thalamo-cortical loop, with a prominent representation in motor cortex. In support of this view, motor cortex recordings in a rodent model of parkinsonism showed a gamma oscillation during dyskinesia, remarkably similar to that reported here (Halje et al., 2012, supra). Together these finding support the hypothesis that oscillations play a fundamental role in brain network dynamics and that alternations of these oscillations may manifest as disease (Voytek and Knight, 2015, Biol Psychiatry 77:1089-1097).

The mechanism by which gamma oscillations lead to dyskinesia is speculative. Oscillations can bias the probability of spike discharge, such that neuronal spiking tends to occur at a preferred oscillatory phase. Gamma oscillations tend to synchronize cortical neuronal pools so that common inputs to a cell arrive in close temporal succession, facilitating activation (Fries et al., 2001; Fries, 2009). In primary motor cortex, "fragments of movement" appear to be encoded by small groups of neurons, as demonstrated by the induction of complex movements by microstimulation (Graziano et al., 2002, Neuron 34:841-851; Hatsopoulos et al., 2007, J Neurosci 27:5105-5114). Thus, the coordination of these neuronal pools by an exaggerated gamma oscillation could release locally encoded fragments in rapid progression to produce choreiform activity.

Striatal Mechanisms of Levodopa Induced Dyskinesia: Possible Links to Gamma Oscillations The cellular origin of levodopa-induced dyskinesia remains controversial, but most current theories, developed in rodent models, emphasize changes in striatal microcircuitry induced by dopamine denervation followed by its unregulated restoration by medication (Fieblinger and Cenci, 2015, Mov Disord 30:484-493). Pulsatile dopamine release may be mediated by serotonergic neurons (Carta et al., 2007, Brain 130:1819-1833). Striatal changes include morphological alternations in glutamatergic synapses onto striatal medium spiny neurons and concomitant changes in long term potentiation and long term depression, which strengthen corticostriatal connections (Fieblinger and Cenci, 2015, supra). These changes might favor activation of striatal cells originating the prokinetic "direct" intrinsic basal ganglia pathway (Thiele et al., 2014, Neurobiology of disease 71:334-344).

A challenge in this field is relating the changes in striatal physiology to oscillatory phenomenon. We and others have proposed that striatal changes in the parkinsonian off-state have the effect of reducing the basal ganglia "filter" of cortical activity, such that normal rhythms, including the motor beta rhythm, are excessively transmitted through the basal ganglia thalamo-cortical loop resulting in aberrant beta synchronization (Weinberger and Dostrovsky, 2011, Neuroreport 22:151-156; de Hemptinne et al., 2013). A similar mechanism could underlie dyskinesia, again due to exaggerated "propagation" of an otherwise normal physiological rhythm through abnormally strengthened corticostriatal synapses.

Entrainment of Gamma Oscillations by Stimulation

Clinically, dyskinesia is not only associated with levodopa in PD, but may be induced by DBS in both PD (Yelnik et al., 2000) and non-PD disorders (Mouton et al., 2006; Mallet et al., 2008; Ostrem et al., 2011). The entrainment of gamma rhythms by DBS (FIG. 14 offers a potential explanation for this. DBS is often delivered at 120-180 Hz, approximately twice the typical frequency of the dyskinesia-associated gamma oscillation. DBS entrains axonal activity to stimulus pulses, but this entrainment does not occur after every pulse (Li et al., 2012). Frequent failures of entrainment (in this case, every other stimulation pulse) could readily result in driving axonal or neuronal activity at 60-90 Hz. Our results suggest that irregular stimulation paradigms may be less pro-dyskinetic than the constant frequency stimulation that is used currently.

Control Signals for Closed Loop DBS

The finding of a brain rhythm reliably associated with dyskinesia has translational potential as a control signal in closed loop DBS (Rosin et al., 2011, Neuron 72:370-384; Little et al., 2013, Annals of neurology 74:449-457). Commercially available DBS systems are "open loop" devices that do not respond to patients' symptom fluctuation. Stimulation induced dyskinesia can be an important dose-limiting effect of DBS (Mouton et al., 2006, Mov Disord 21:1771-1773; Mallet et al., 2008, The New England journal of medicine 359:2121-2134; Ostrem et al., 2011, Neurology 76:870-878.). To address this, a system could be designed that sensed the gamma rhythm and dynamically adjusted stimulation parameters to keep motor cortical spectral power in the relevant bandwidth below a specified level, mitigating hyperkinetic adverse effects. The cortical sensor provides a signal that is easily separable from normal cortical oscillatory activity, and has less stimulation artifact than signals detected from the DBS lead. Control signals for closed loop DBS related to akinesia, based on activity in the beta band, are under exploration (Little et al., 2013, supra). However, beta activity is strongly affected by voluntary movement (Crone et al., 1998b, supra; de Hemptinne et al., 2015, supra) which may present a challenge for its use in closed loop DBS.

Determining the specificity of the gamma oscillation for dyskinesia depends on the accuracy of dyskinesia detection. In-clinic scoring was performed by a movement disorders neurologist, but the relative insensitivity of the scoring system and difficulty of continuously assessing dyskinesia during brain recording, precluded precise examination of the timing of neural activity relative to changes in dyskinesia severity. Since dyskinesia is not always present during study visits, we chose to increase our number of recordings by allowing patients to trigger recordings at home. A cognitively intact PD patient with a history of dyskinesia is capable of scoring dyskinesia as present or absent, but we do not have independent verification of dyskinesia for home recordings. Additionally, because we utilized an implant without micro-recording capability, our study focused on network rhythms recorded from macro-electrodes and did not address the relationship between dyskinesia and single unit discharge. However, it is likely that gamma oscillations exert a strong effect on neuronal discharge by entrainment to a preferred phase of the gamma rhythm (Trottenberg et al., 2006, supra; Halje et al., 2012,supra).

Using multi-site chronic brain recordings in humans with PD, we characterize the association of a gamma oscillation in the basal ganglia-cortical motor network with dyskinesia. These findings illuminate the network dynamics underlying dyskinesia, and suggest a strategy for feedback-controlled DBS.

Example 2

Figure 15:
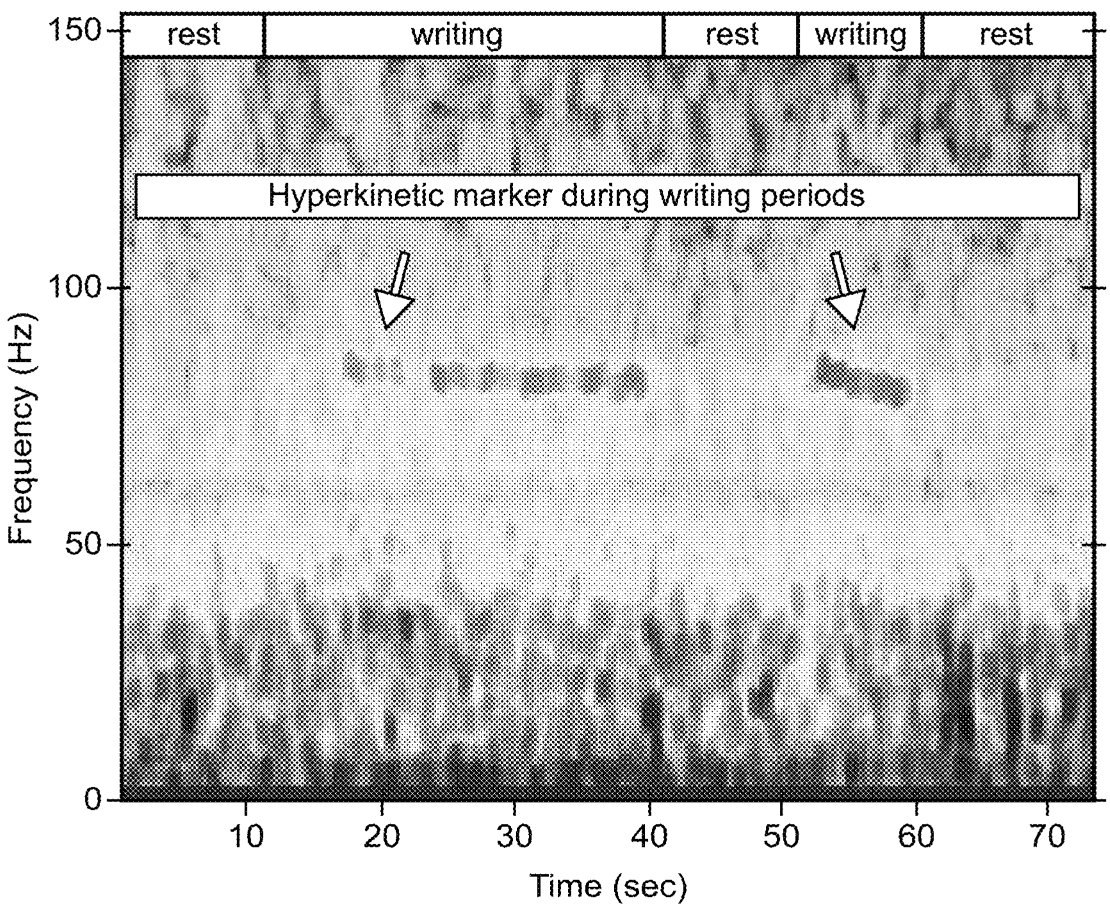
FIG. 15 depicts cortical potentials recorded during periods of rest and periods of writing in a dystonia patient.

Excessive movement disorders such as dyskinesia (see Example 1) or dystonia are can be identified based on brain activity. Cortical potentials were recorded during periods of rest and periods of writing, which elicited hyperkinetic dystonic symptoms, in a dystonia patient. A time-frequency plot (spectrogram) of field potentials recorded from the surface of the primary cortex of the dystonia patient is depicted in FIG. 15. Frequency in the range of 60-90 Hz provides a marker for hyperkinetic state of the dystonia patient during periods of writing.

Methods:

A patient with dystonia underwent deep brain stimulation implantation for the treatment of his symptoms that were not adequately controlled by medications. Prior to surgery, he consented to be part of our intraoperative study. At the beginning of the surgery, a 6-contact electrocorticography (ECoG) electrode was inserted, through the burr hole made to implant deep brain stimulation electrode, and temporarily placed over the sensorimotor cortex. Cortical field potentials were then recorded intraoperatively while the patient was awake and either resting or engaged in a task including hand movement, arm movement, and writing that exacerbated patient's symptoms. Brain signals were then analyzed off-line, in the frequency domain, and for each ECoG contact, the power spectral density (PSD) and spectral power over time were computed.

FIG. 15 shows the spectral power over time of the motor cortex field potentials during periods of rest and periods of writing. FIG. 15 shows increased activity in the gamma band (~82 Hz) during periods of writing, which are associated with worsening of symptom severity. Periods of rest with milder symptoms were not associated with this excessive oscillatory activity. This increase gamma activity was specific to the sensorimotor cortex and was stronger in contacts covering the primary motor cortex. These results are very similar to those observed in PD patients experiencing dyskinesia, involuntary movements induced by medication or electrical stimulation. FIG. 15 shows that excessive oscillatory activity in the gamma band (60-90 Hz) reflects a hyperkinetic state.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a movement disorder in a human patient, the method comprising:

recording first electrical activity as a function of time with one or more recording leads, wherein each of the one or more recording leads used to record the first electrical activity is placed at the motor cortex, wherein the patient is receiving a treatment for the movement disorder;

performing a frequency domain transformation of the first electrical activity;

analyzing a set of frequency values in the range of 60 Hz to 90 Hz from the transformed first electrical activity; and modifying the treatment of the patient only when the analyzed set of frequency values has oscillatory activity in the range of 60 Hz to 90 Hz in the motor cortex in order to thereby decrease oscillatory activity in the range of 60 Hz to 90 Hz in the motor cortex, wherein oscillatory activity in the range of 60 Hz to 90 Hz is indicative of hyperkinetic state in the patient, wherein the treatment comprises deep brain stimulation (DBS), and wherein modifying the treatment comprises adjusting a parameter of DBS.

2. The method of claim 1, wherein the oscillatory activity comprises field potential.

3. The method of claim 1, wherein the recording first electrical activity comprises performing chronic electrocorticography (ECOG).

4. The method of claim 1, wherein the parameter of DBS is selected from the group consisting of contact choice, amplitude, pulse width, and frequency of stimulation.

5. The method of claim 1, wherein adjusting the DBS parameter comprises stimulating the dorsal subthalamic nucleus (STN).

6. The method of claim 1, wherein the movement disorder is Parkinson's disease.

7. The method of claim 1, wherein the movement disorder is essential tremor.

8. The method of claim 1, wherein the movement disorder is dystonia.

9. The method of claim 1, wherein the movement disorder is Huntington's disease.

10. The method of claim 1, wherein the movement disorder is Tourette syndrome.

11. The method of claim 1, wherein the patient has Parkinson's disease and dyskinesia.

12. The method of claim 1, wherein the patient has Parkinson's disease and levodopa-induced dyskinesia.

13. The method of claim 1, wherein the oscillatory activity is in the basal ganglia-thalamo-cortical motor loop.

14. The method of claim 1, wherein the recording is performed with the one or more recording leads placed at the primary motor cortex (M1).

* * * * *